United States Patent
Lee et al.

(10) Patent No.: US 11,381,417 B2
(45) Date of Patent: Jul. 5, 2022

(54) USER TERMINAL AND SLEEP MANAGEMENT METHOD

(71) Applicant: Samsung Electronics Co., Ltd, Suwon-si (KR)

(72) Inventors: Ki Sup Lee, Seongnam-si (KR); Hyun Cheol Oh, Suwon-si (KR); Kyung Nam Kim, Incheon (KR); Yeon A Hwang, Suwon-si (KR); Dong Hyuk Shin, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 557 days.

(21) Appl. No.: 15/757,313

(22) PCT Filed: Aug. 29, 2016

(86) PCT No.: PCT/KR2016/009594
§ 371 (c)(1),
(2) Date: Mar. 2, 2018

(87) PCT Pub. No.: WO2017/039264
PCT Pub. Date: Mar. 9, 2017

(65) Prior Publication Data
US 2019/0074988 A1    Mar. 7, 2019

(30) Foreign Application Priority Data
Sep. 3, 2015    (KR) .................. 10-2015-0124571

(51) Int. Cl.
*A61B 5/00*    (2006.01)
*H04L 12/28*    (2006.01)
(Continued)

(52) U.S. Cl.
CPC .......... *H04L 12/282* (2013.01); *A61B 5/0002* (2013.01); *A61B 5/0004* (2013.01);
(Continued)

(58) Field of Classification Search
CPC ...... A61M 21/02; A61B 5/024; A61B 5/4812; G05B 13/00
See application file for complete search history.

(56) References Cited

U.S. PATENT DOCUMENTS 7,956,755 B2    6/2011    Lee et al.
8,409,074 B2    4/2013    Arai et al.
(Continued)

FOREIGN PATENT DOCUMENTS

CN    102043385 A    5/2011
CN    102840645 A    12/2012
(Continued)

OTHER PUBLICATIONS

International Search Report dated Dec. 6, 2016 in connection with International Patent Application No. PCT/KR2016/009594.
(Continued)

*Primary Examiner* — Kaylee R Wilson

(57) ABSTRACT

Disclosed herein are a sleep management method includes obtaining sleep data of a user, obtaining a sleep state of the user on the basis of the sleep data, and controlling at least one home appliance on the basis of the sleep state of the user, and the sleep data includes signals corresponding to a heart rate, respiration rate, and movement of the user detected by a piezoelectric sensor.

7 Claims, 30 Drawing Sheets

(51) Int. Cl.
  *A61B 5/024* (2006.01)
  *A61B 5/08* (2006.01)
  *A61B 5/11* (2006.01)
(52) U.S. Cl.
  CPC ............ *A61B 5/024* (2013.01); *A61B 5/0816* (2013.01); *A61B 5/1118* (2013.01); *A61B 5/4809* (2013.01); *A61B 5/6891* (2013.01); *A61B 5/6892* (2013.01); *A61B 5/4812* (2013.01); *A61B 5/4815* (2013.01)

(56) References Cited

U.S. PATENT DOCUMENTS

| | | | |
|---|---|---|---|
| 8,708,904 B2 | 4/2014 | Stivoric et al. | |
| 9,046,414 B2 | 6/2015 | Fadell et al. | |
| 2007/0083079 A1* | 4/2007 | Lee | A61B 5/4806 600/27 |
| 2008/0295531 A1* | 12/2008 | Song | F24F 11/62 62/157 |
| 2012/0103556 A1 | 5/2012 | Lee | |
| 2013/0267791 A1 | 10/2013 | Halperin et al. | |
| 2014/0371635 A1 | 12/2014 | Shinar et al. | |
| 2015/0258301 A1* | 9/2015 | Trivedi | A61B 5/6898 600/28 |
| 2016/0015315 A1* | 1/2016 | Auphan | A61B 5/6892 600/301 |
| 2016/0058429 A1* | 3/2016 | Shinar | A61B 5/02405 600/551 |
| 2016/0151603 A1* | 6/2016 | Shouldice | A61B 5/486 600/28 |
| 2016/0300474 A1* | 10/2016 | Warren | G08B 25/14 |
| 2021/0119554 A1 | 4/2021 | Kim et al. | |

FOREIGN PATENT DOCUMENTS

| | | |
|---|---|---|
| CN | 103822332 A | 5/2014 |
| CN | 203802442 U | 9/2014 |
| CN | 104813378 A | 7/2015 |
| CN | 104879887 A | 9/2015 |
| JP | 2012202659 A | 10/2012 |
| KR | 10-2005-0055072 A | 6/2005 |
| KR | 10-2007-0039331 A | 4/2007 |
| KR | 10-2007-0055608 A | 5/2007 |
| KR | 10-2011-0032605 A | 3/2011 |
| KR | 10-2021-0045661 A | 5/2012 |
| KR | 10-2012-0131253 A | 12/2012 |
| KR | 10-2015-0032106 A | 3/2015 |

OTHER PUBLICATIONS

Written Opinion of the International Searching Authority dated Dec. 6, 2016 in connection with International Patent Application No. PCT/KR2016/009594.
Supplementary European Search Report dated Aug. 28, 2018 in connection with European Patent Application No. 16 84 2230, 8 pages.
Office Action dated Jun. 17, 2020 in connection with Chinese Patent Application No. 201680051164.4, 23 pages.
Intellectual Property India, "Examination report under sections 12 & 13 of the Patents Act, 1970 and the Patents Rules, 2003", dated Feb. 3, 2021 in connection to Indian Patent Application No. 201817007730, 7 pages.
The Second Office Action dated May 7, 2021, in connection with Chinese Patent Application No. 201680051164.4, 18 pages.
Notification of Reason for Refusal dated Aug. 30, 2021 in connection with Korean Patent Application No. 10-2015-0124571, 10 pages.
The Third Office Action dated Nov. 24, 2021, in connection with Chinese Application No. 201680051164.4, 19 pages.
Summons to attend oral proceedings pursuant to Rule 115(1) EPC dated Feb. 18, 2022, in connection with European Application No. 16842230.1, 6 pages.

* cited by examiner

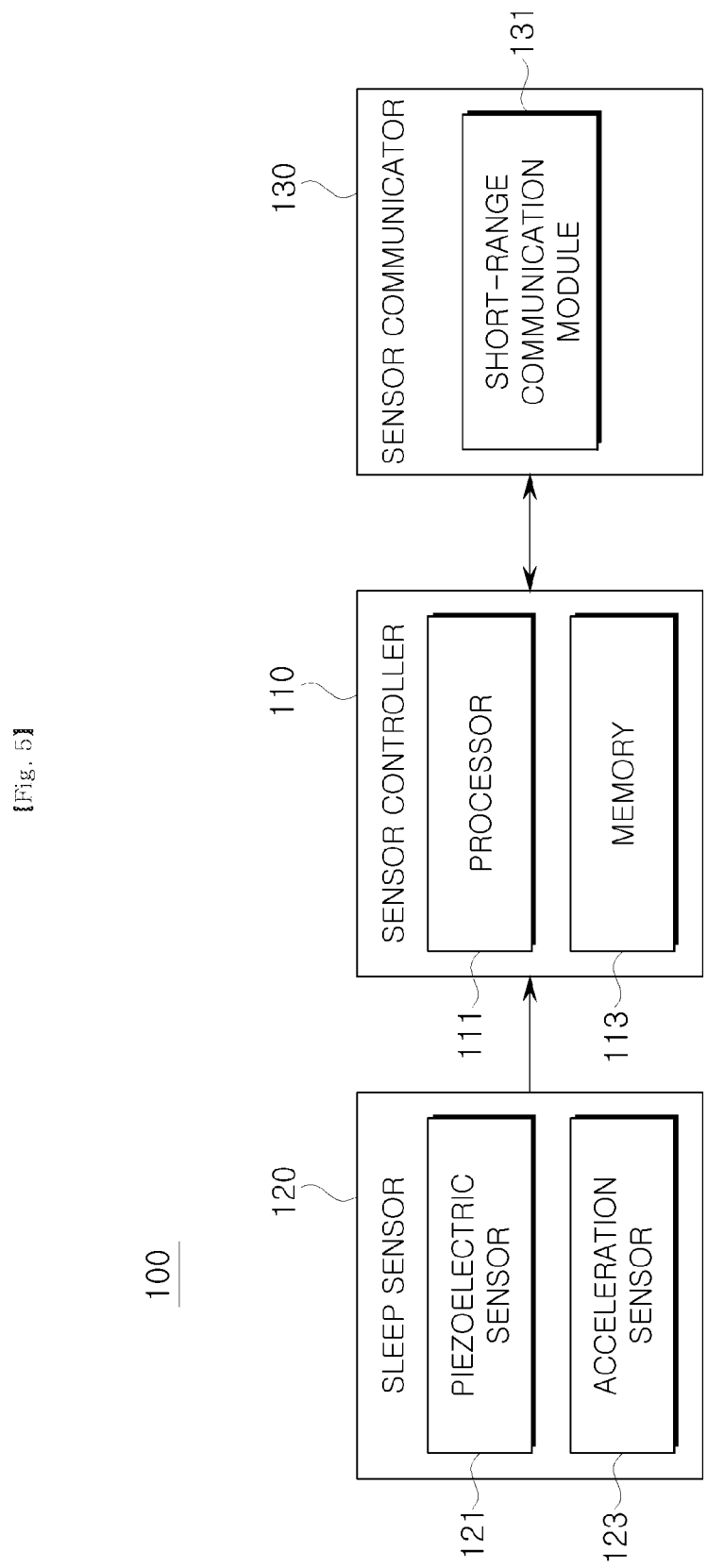
[Fig. 5]

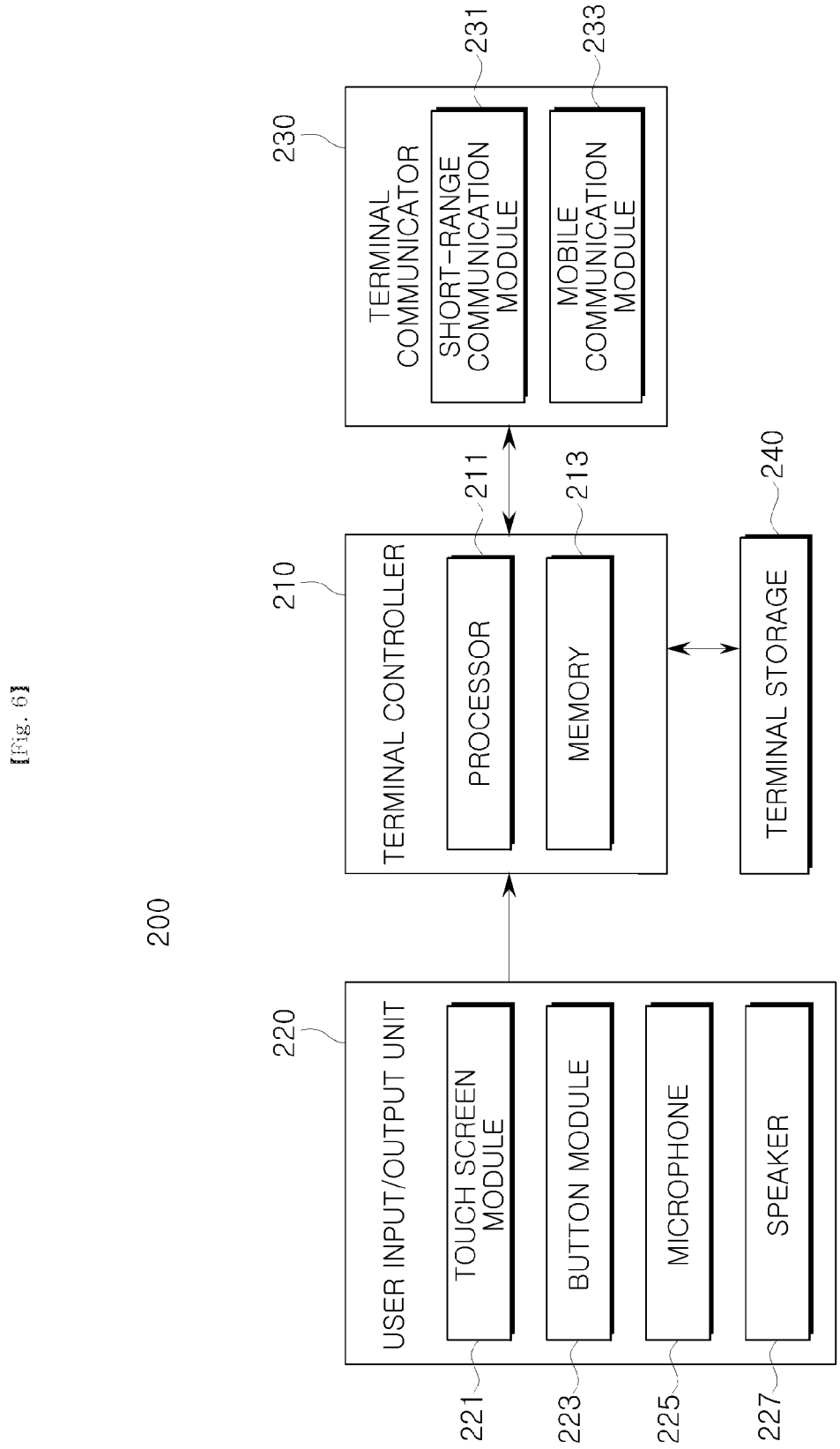
[Fig. 6]

[Fig. 7]
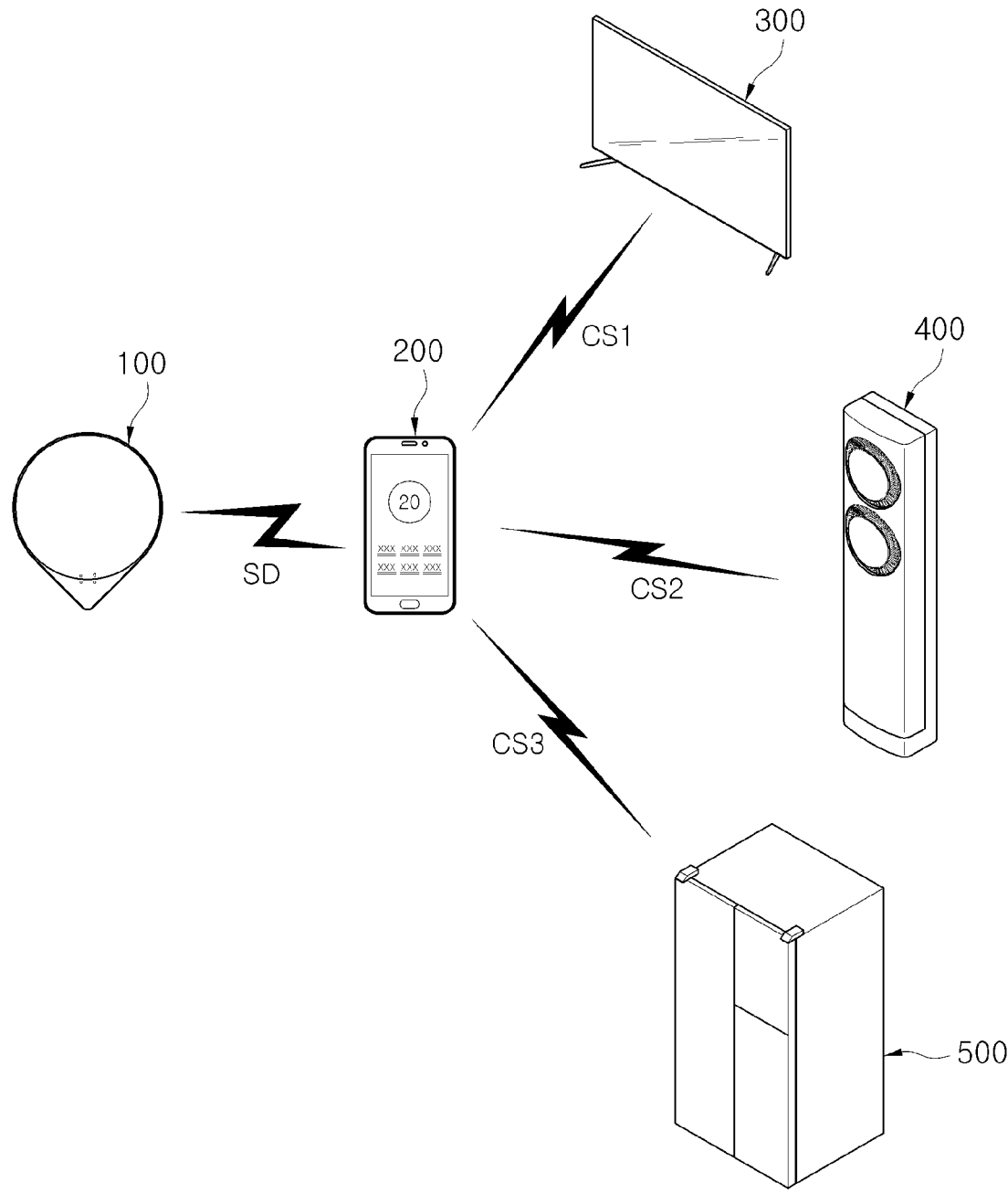

[Fig. 8]
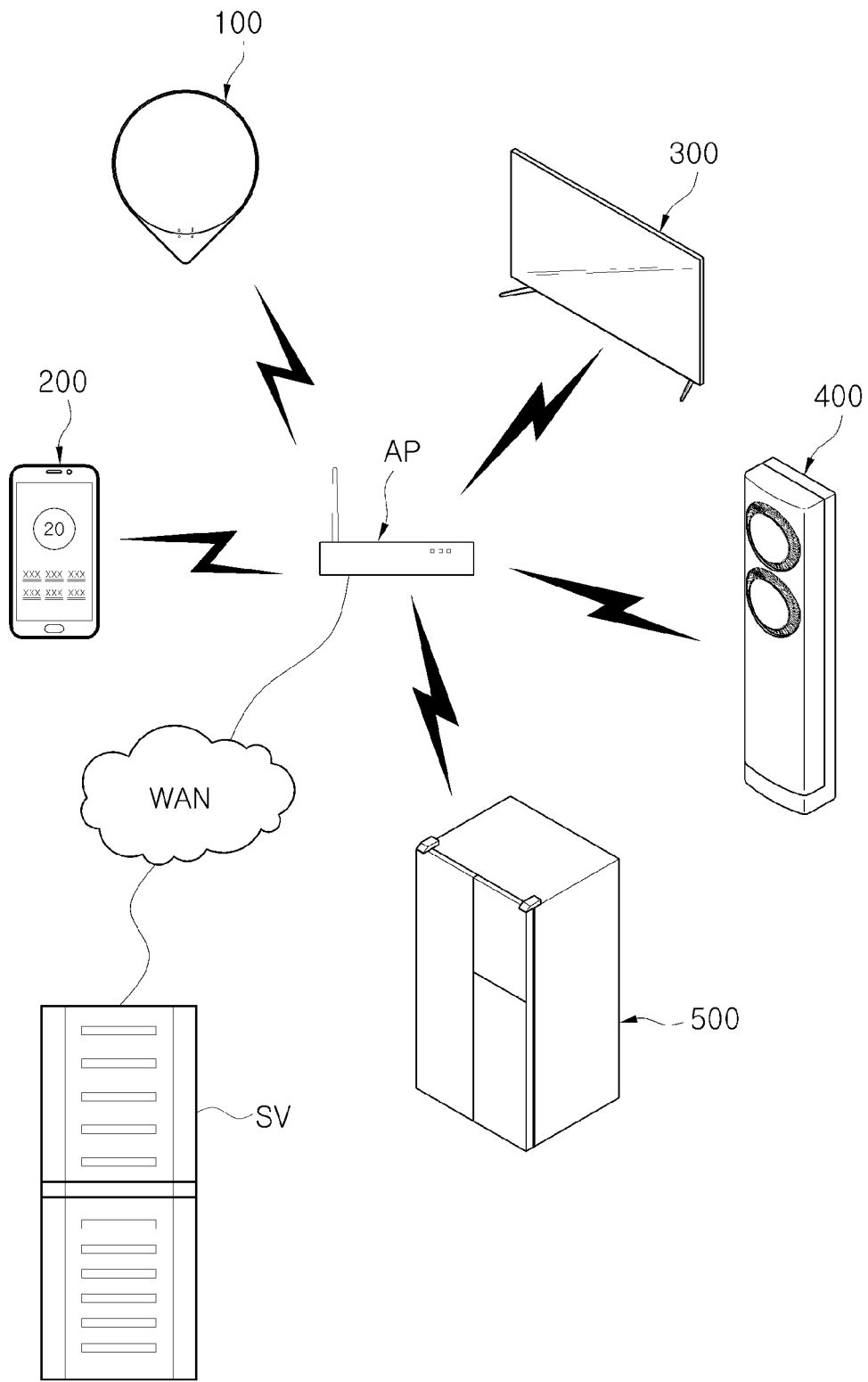

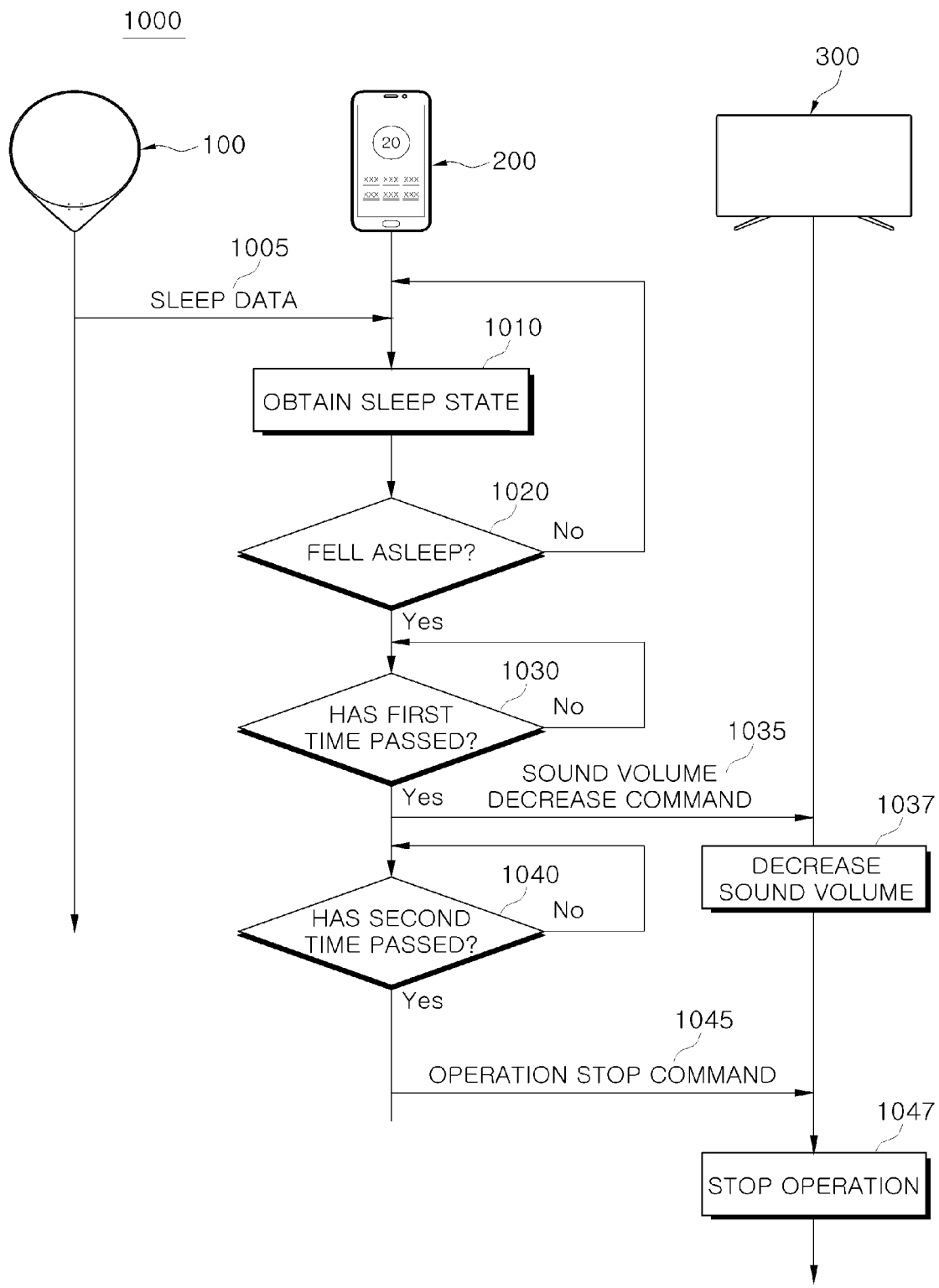
[Fig. 9]

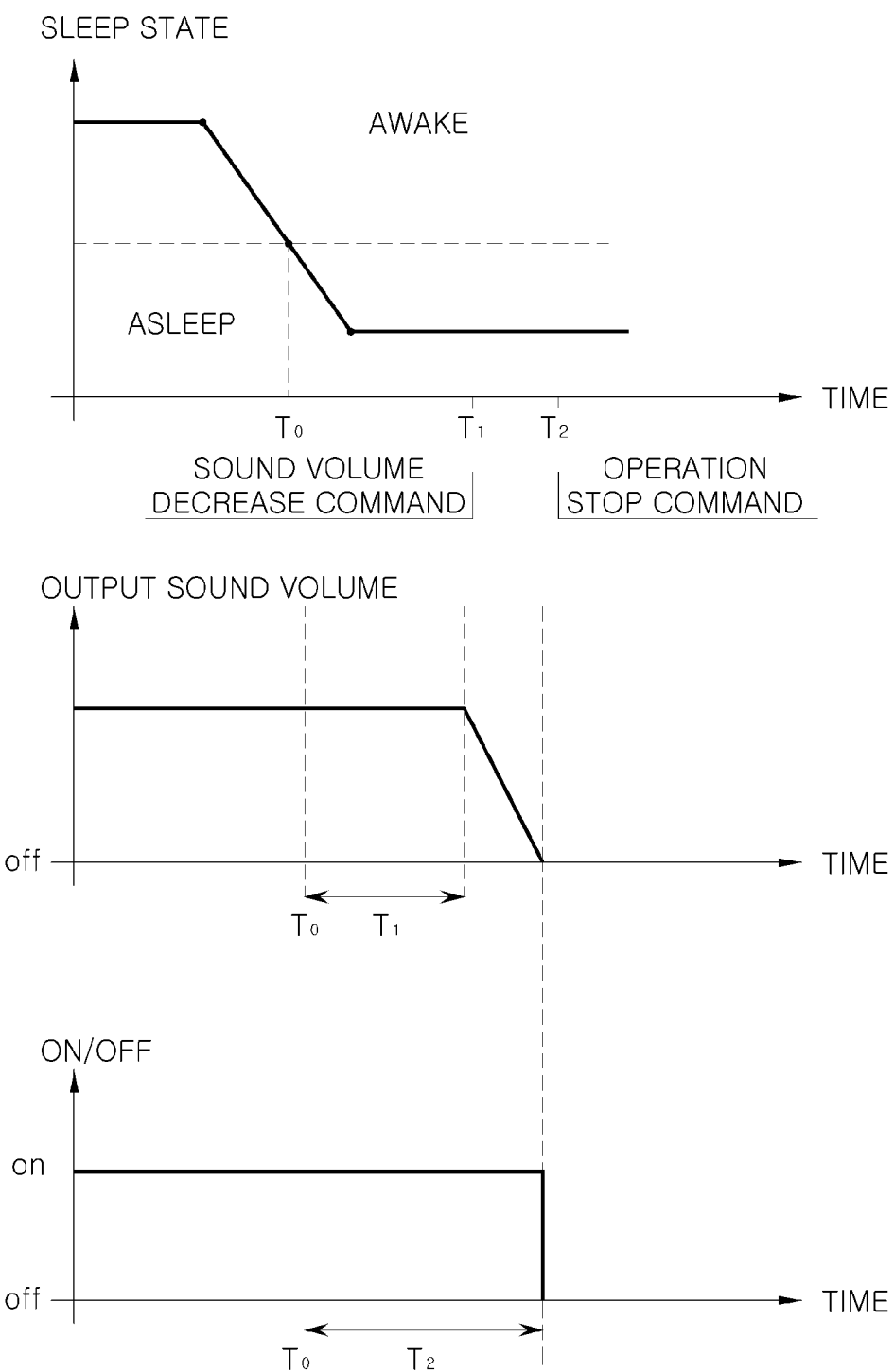

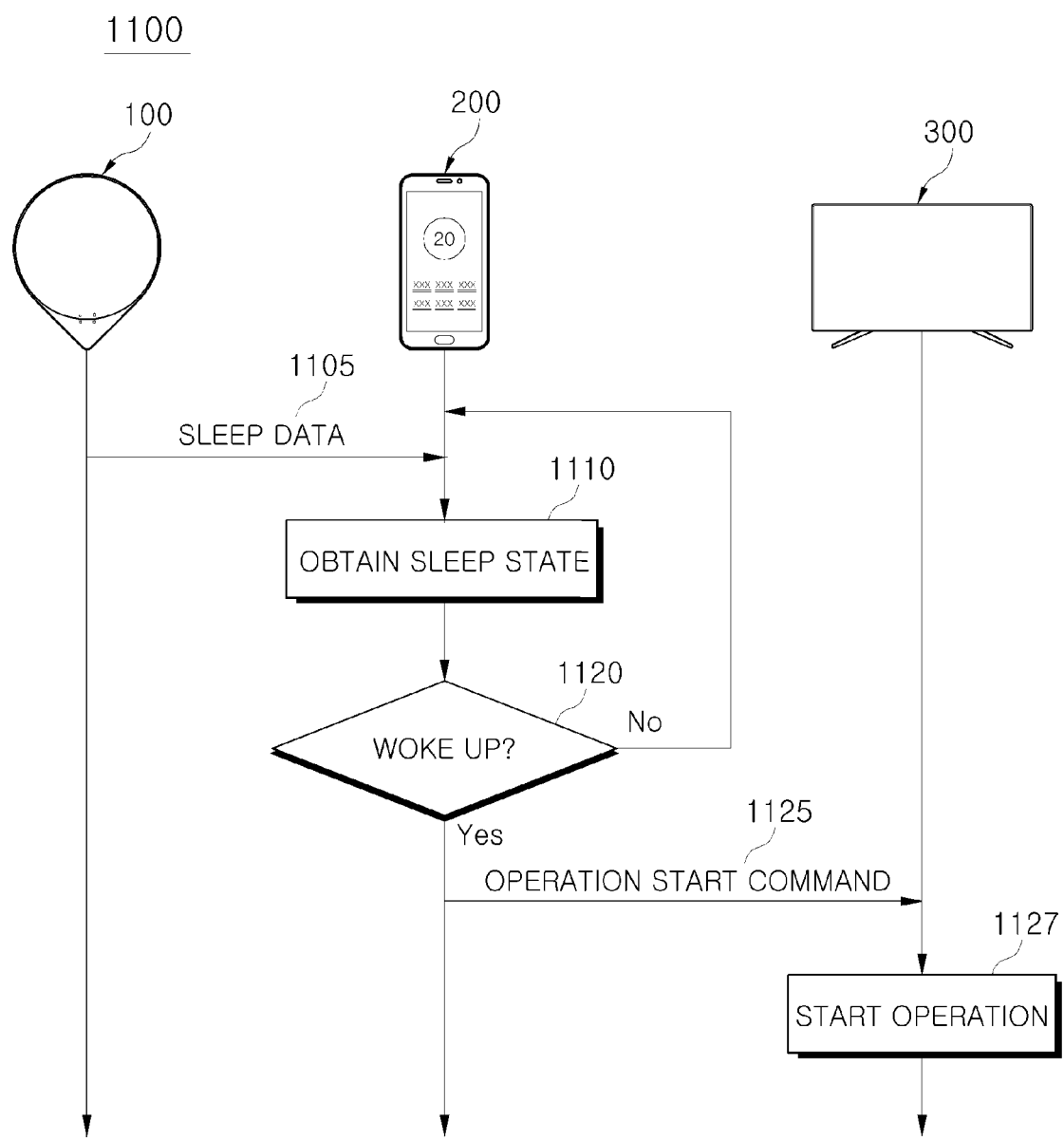
[Fig. 11]

[Fig. 12]
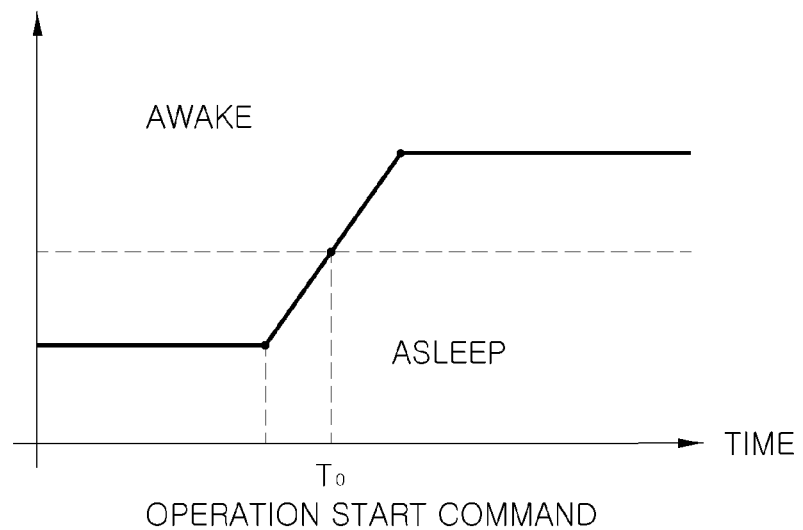
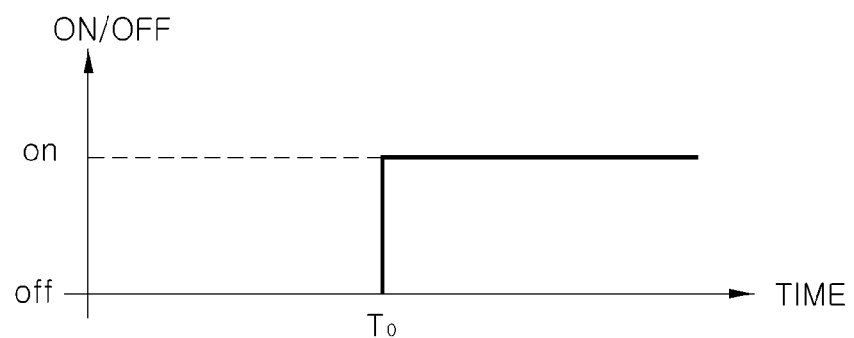

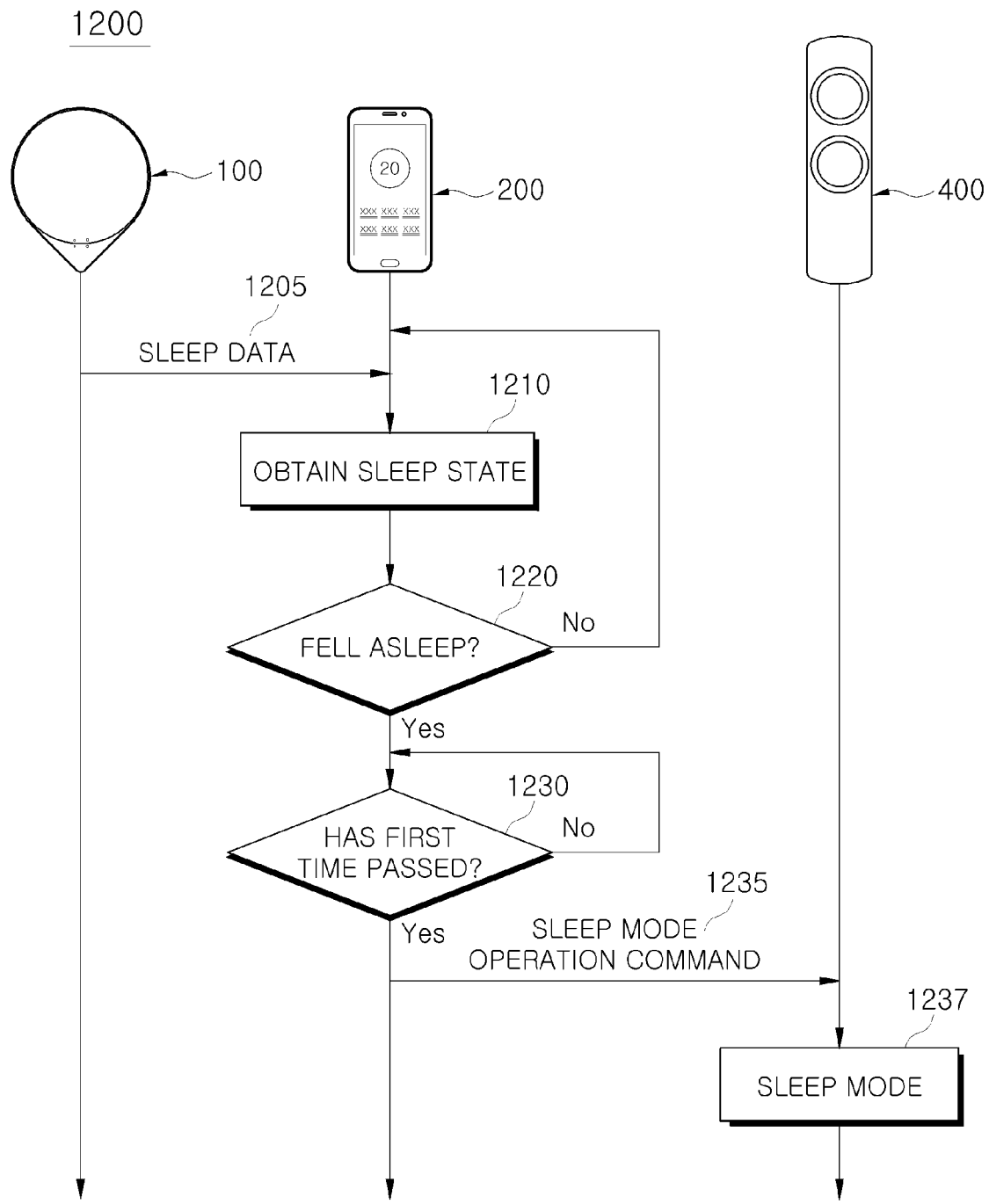
[Fig. 13]

[Fig. 14]
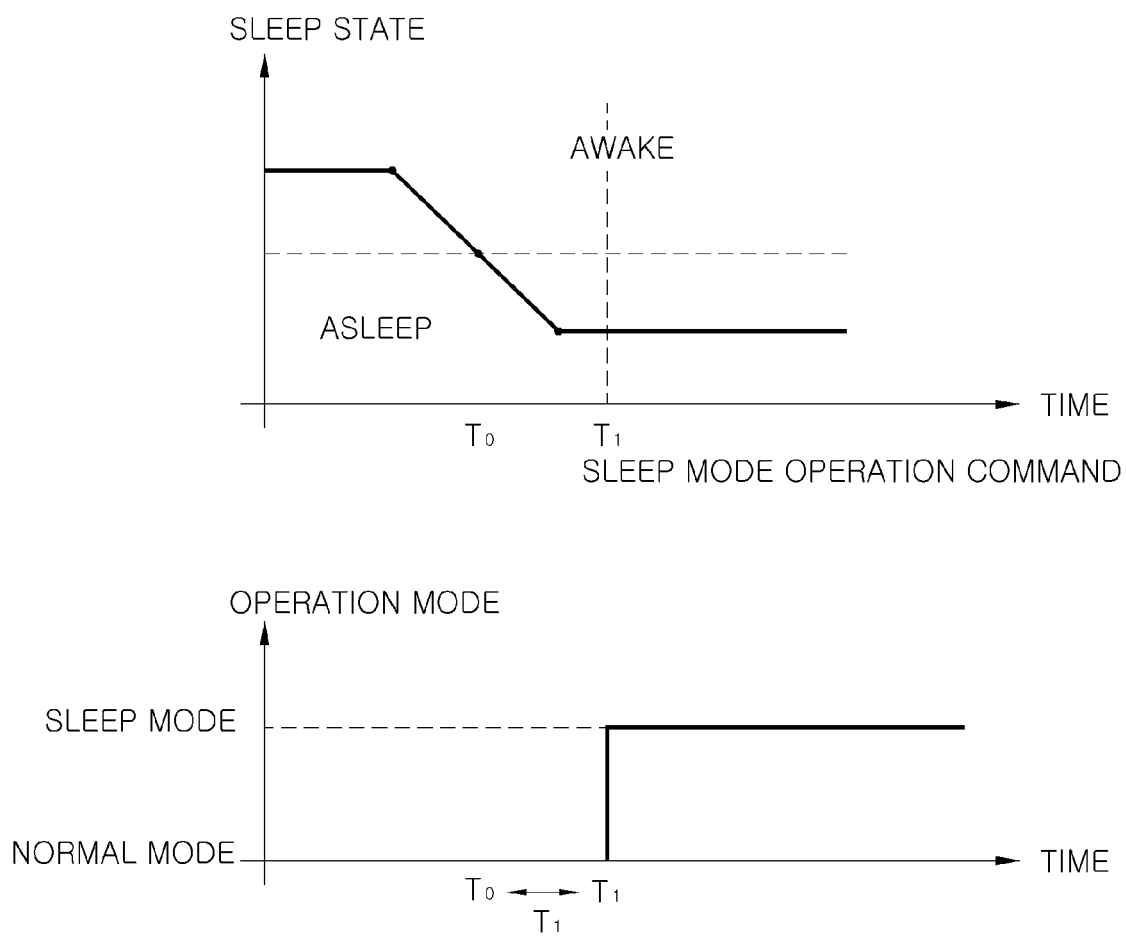

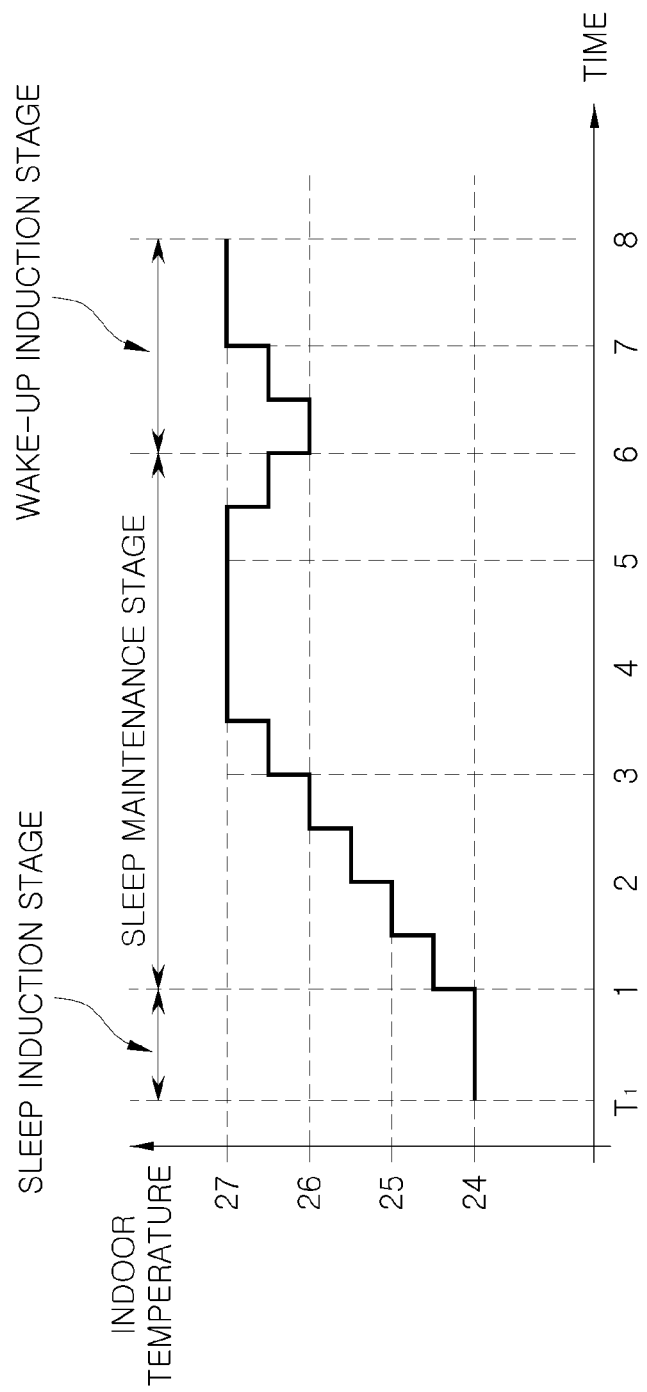

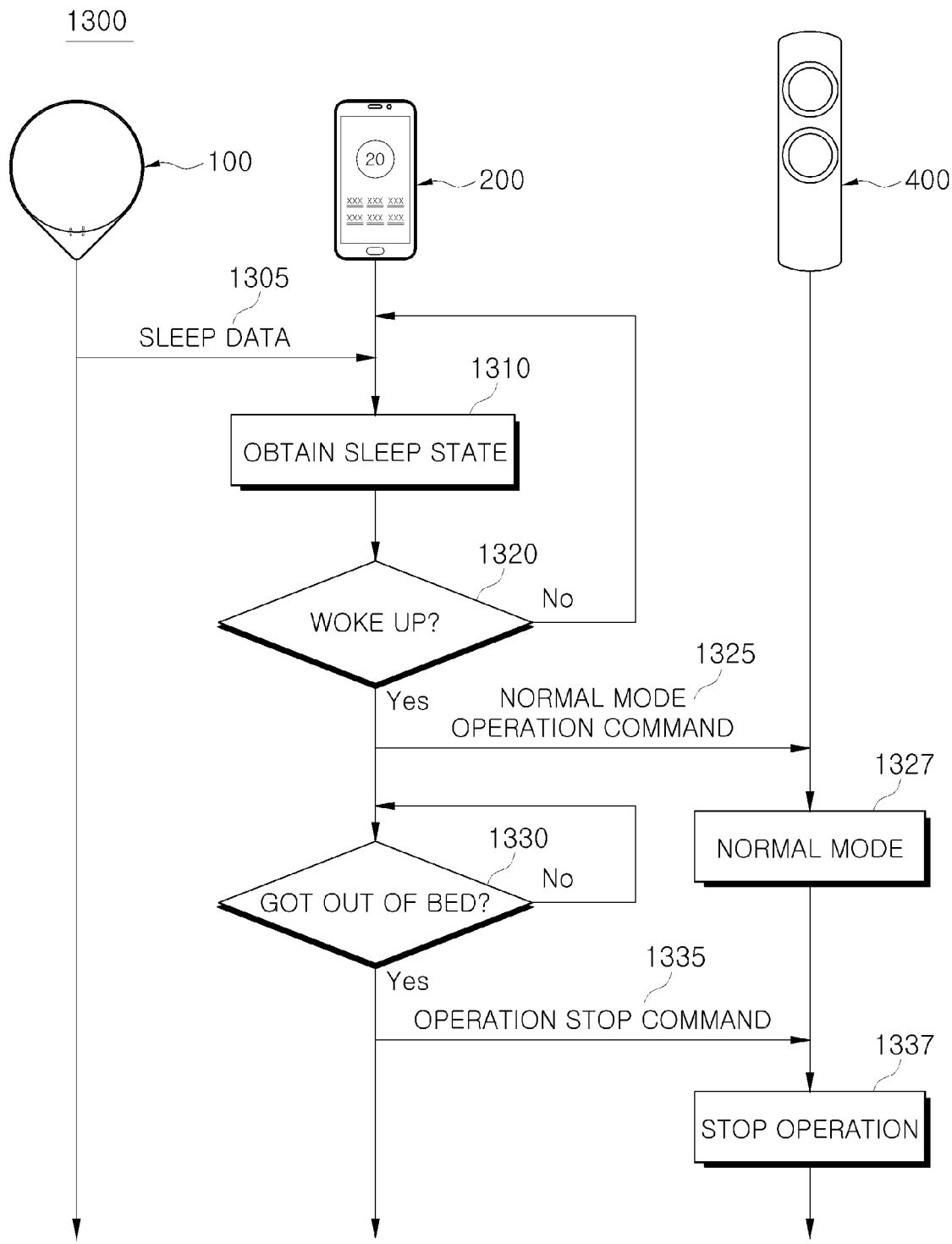
[Fig. 16]

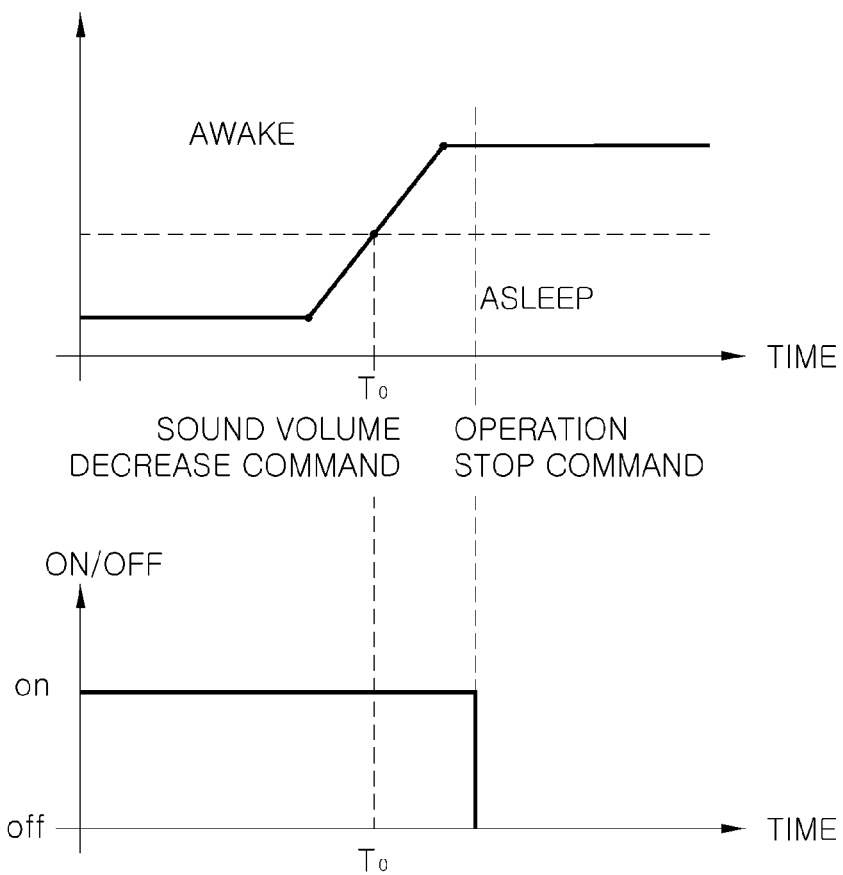

[Fig. 18]
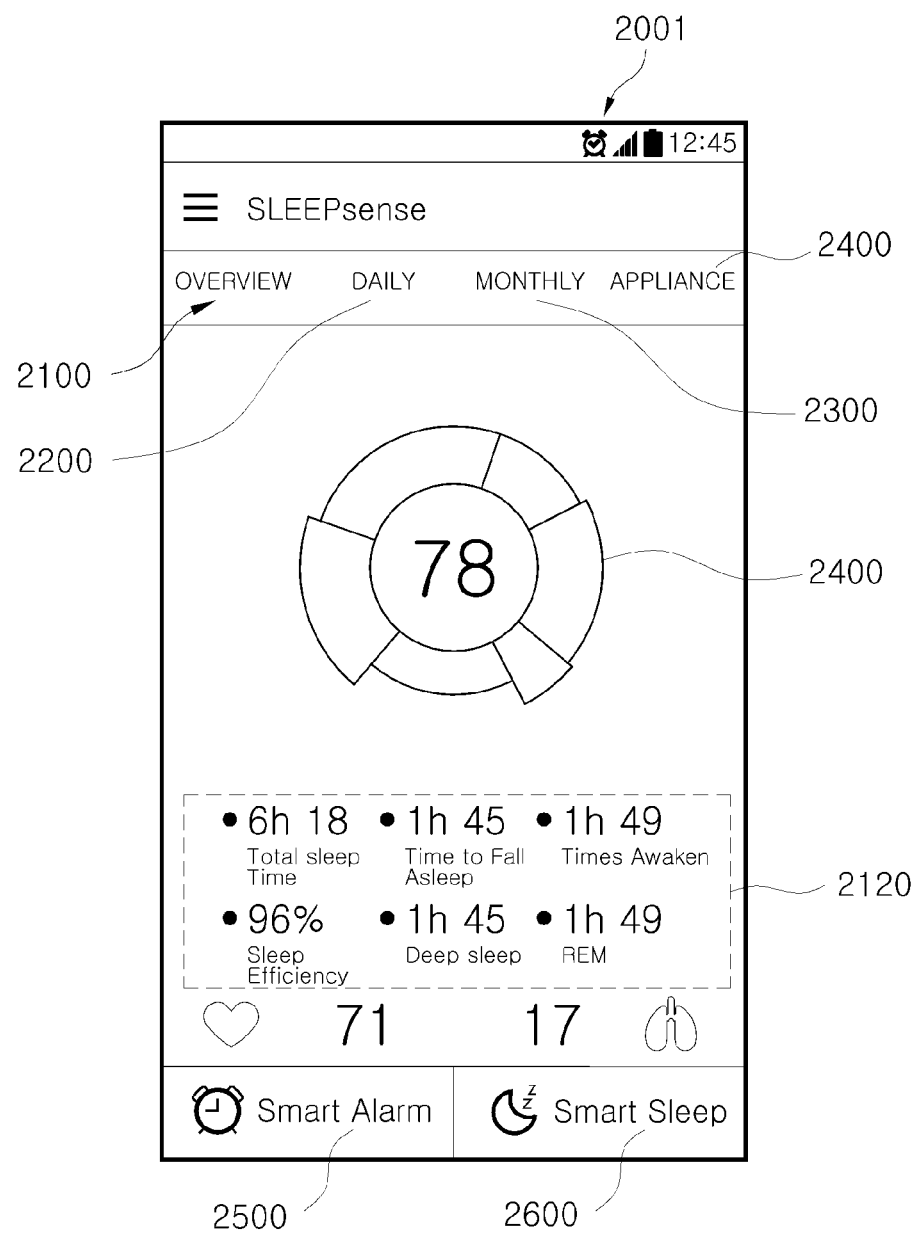

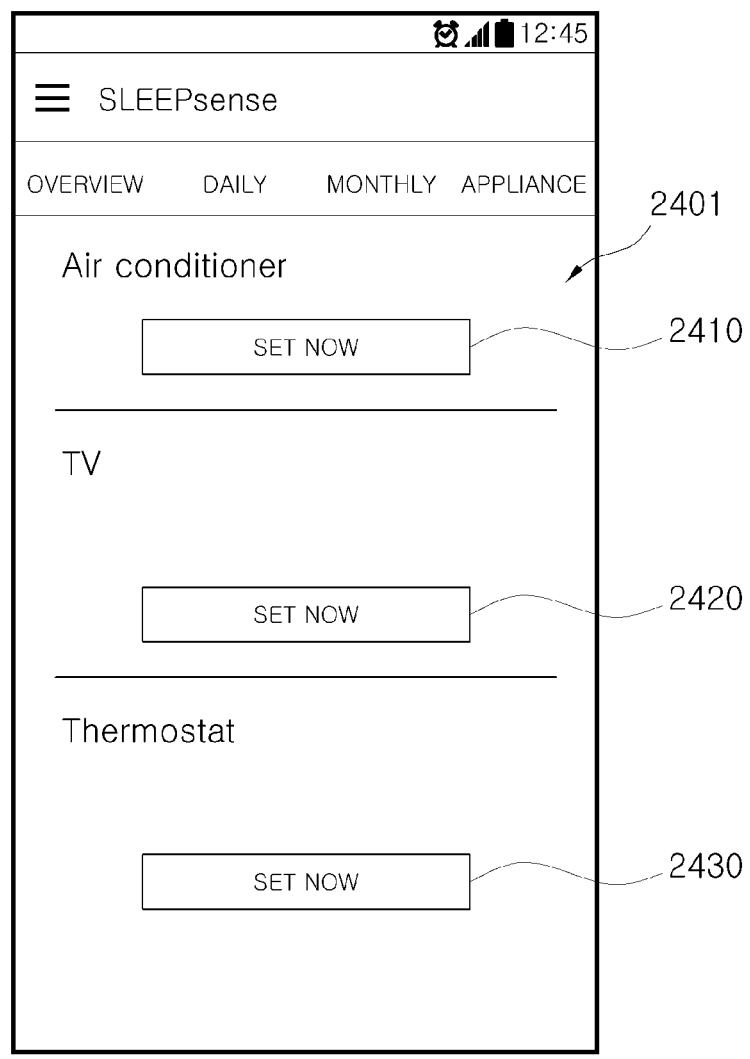

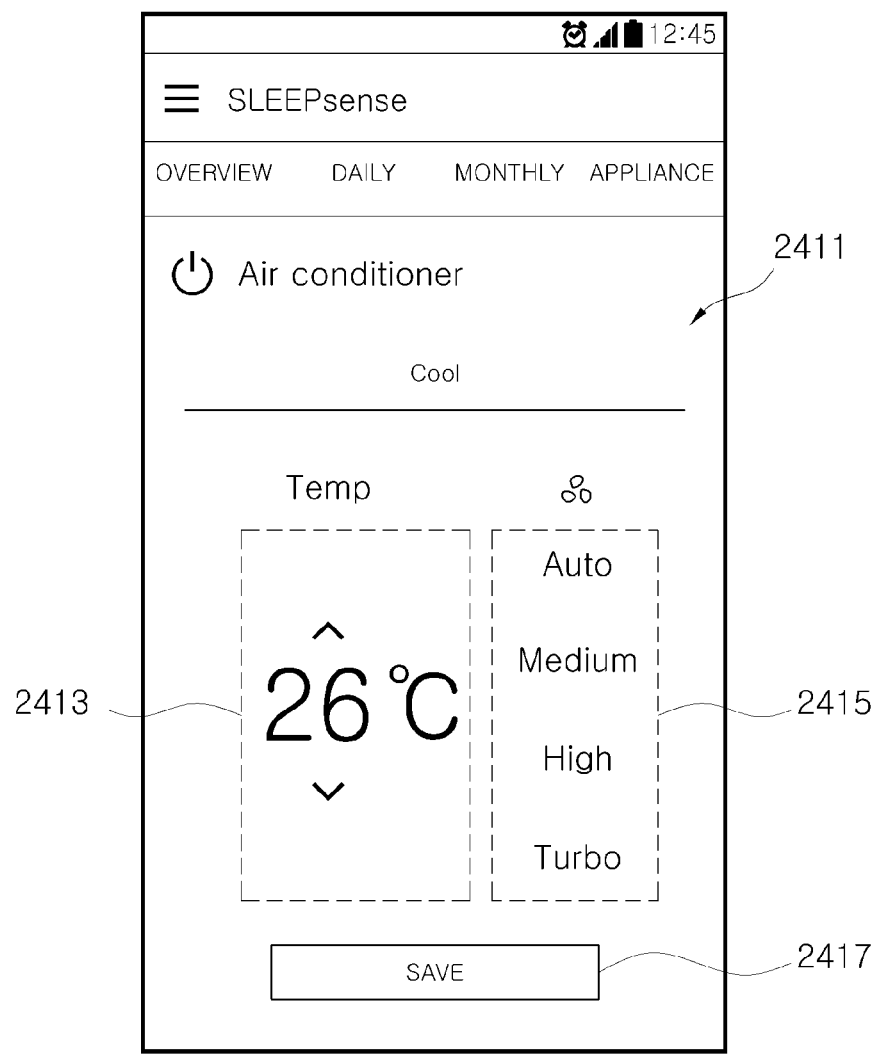
[Fig. 20]

[Fig. 21]
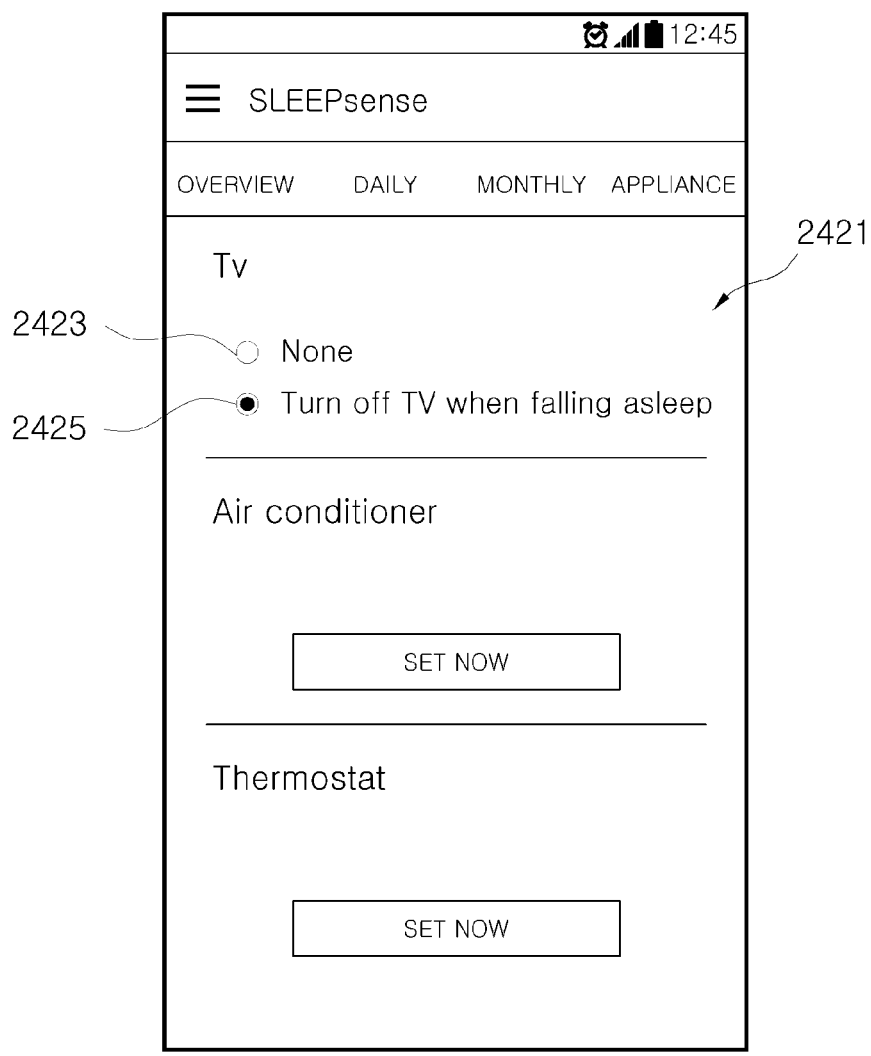

[Fig. 22]
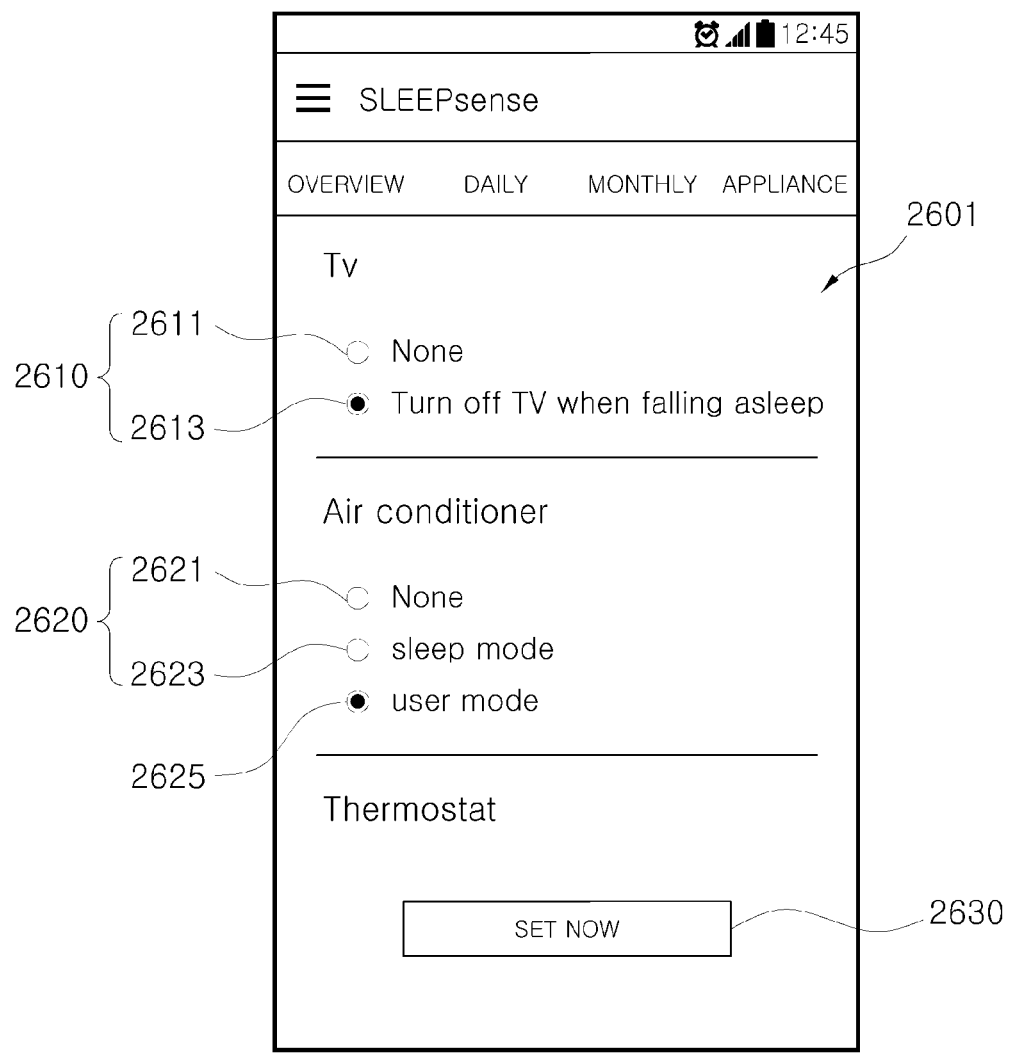

[Fig. 23]
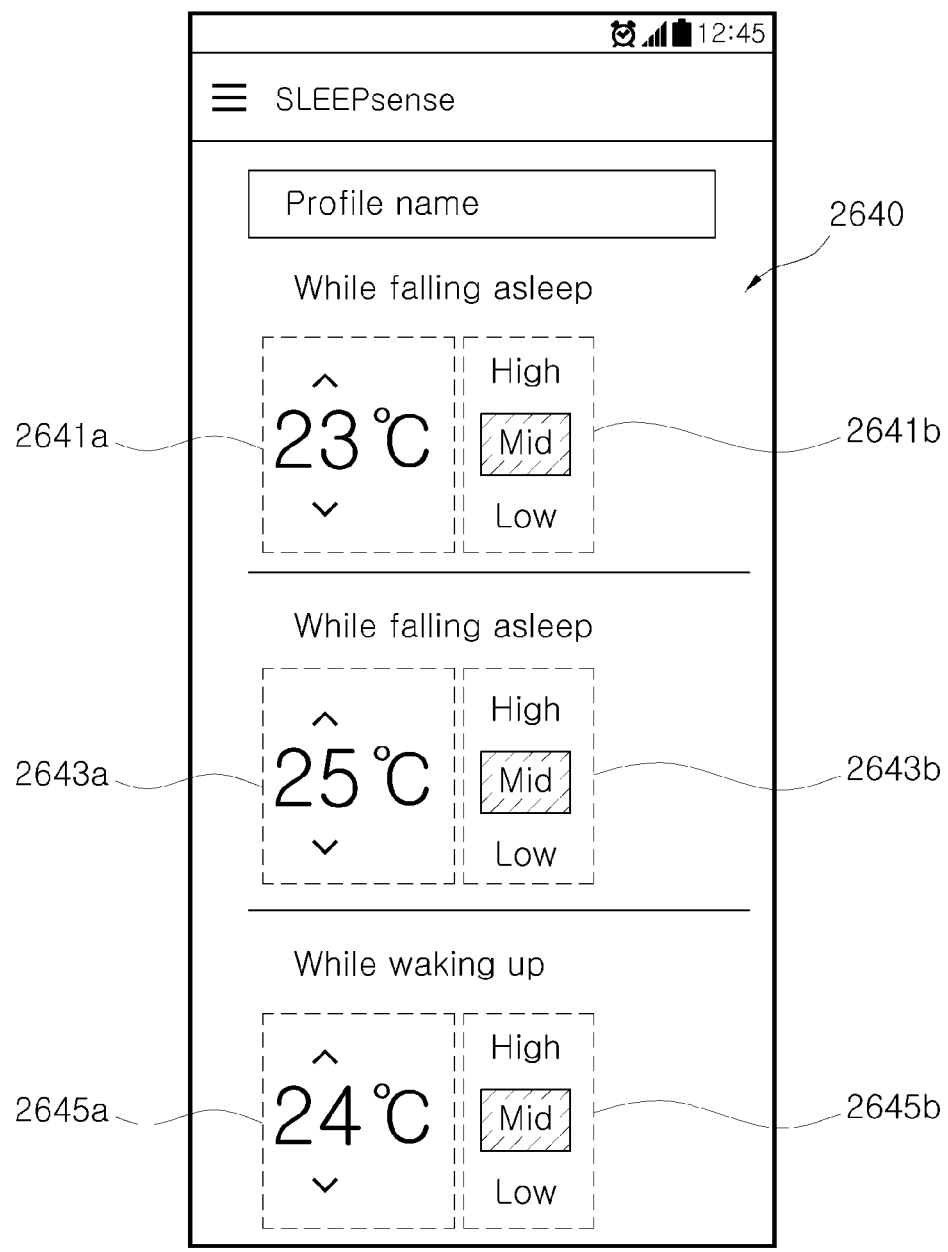

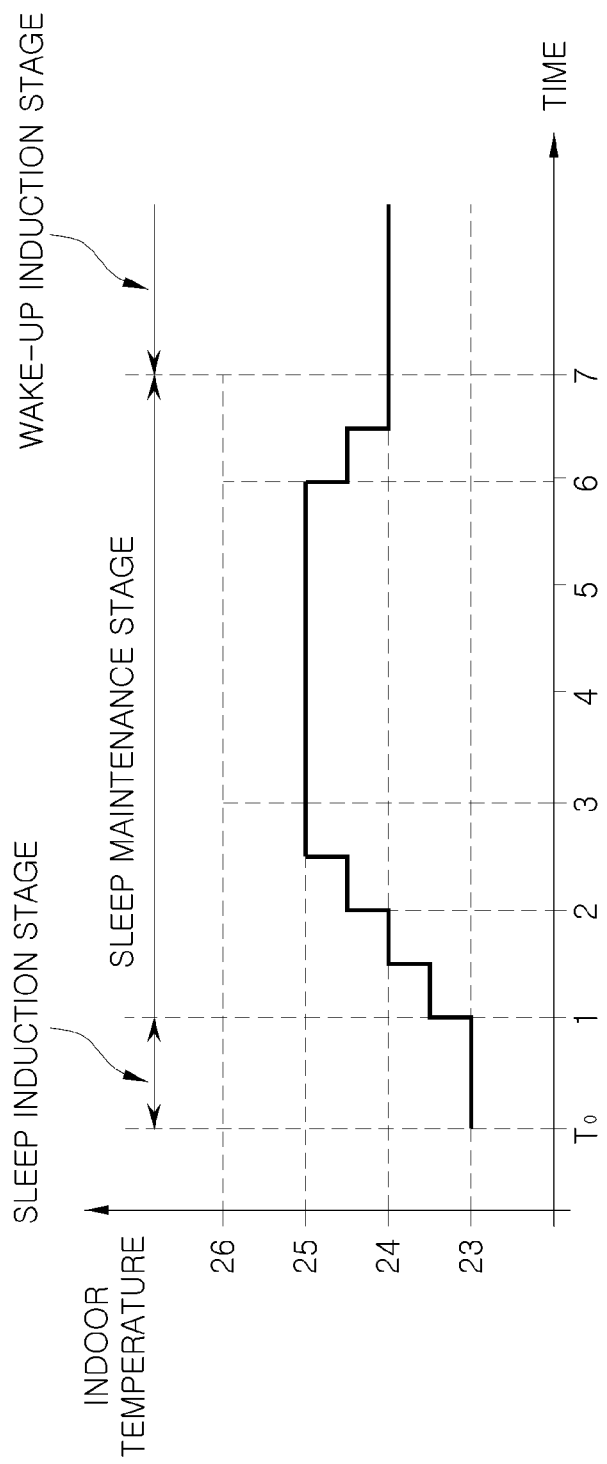
[Fig. 24]

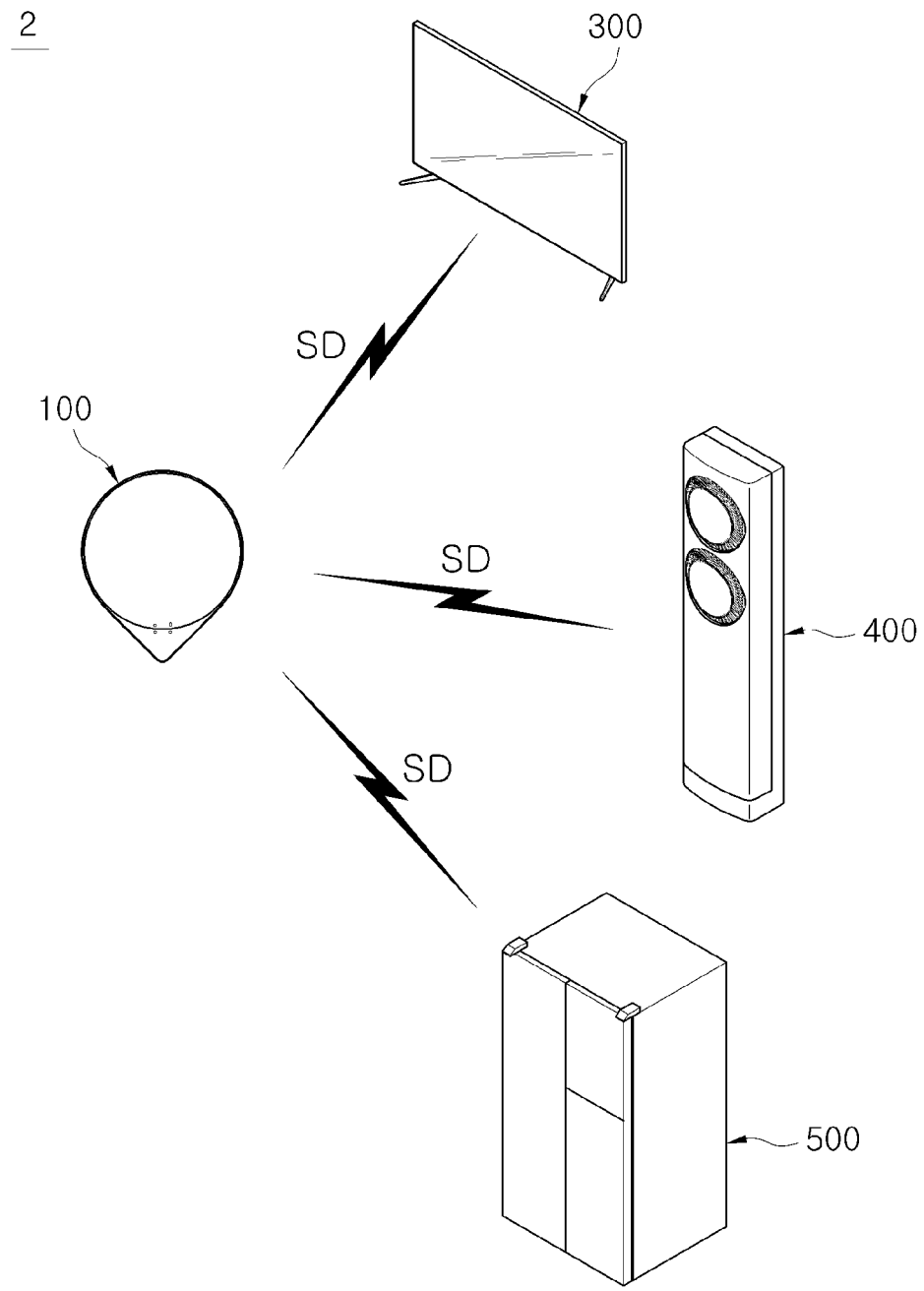
[Fig. 25]

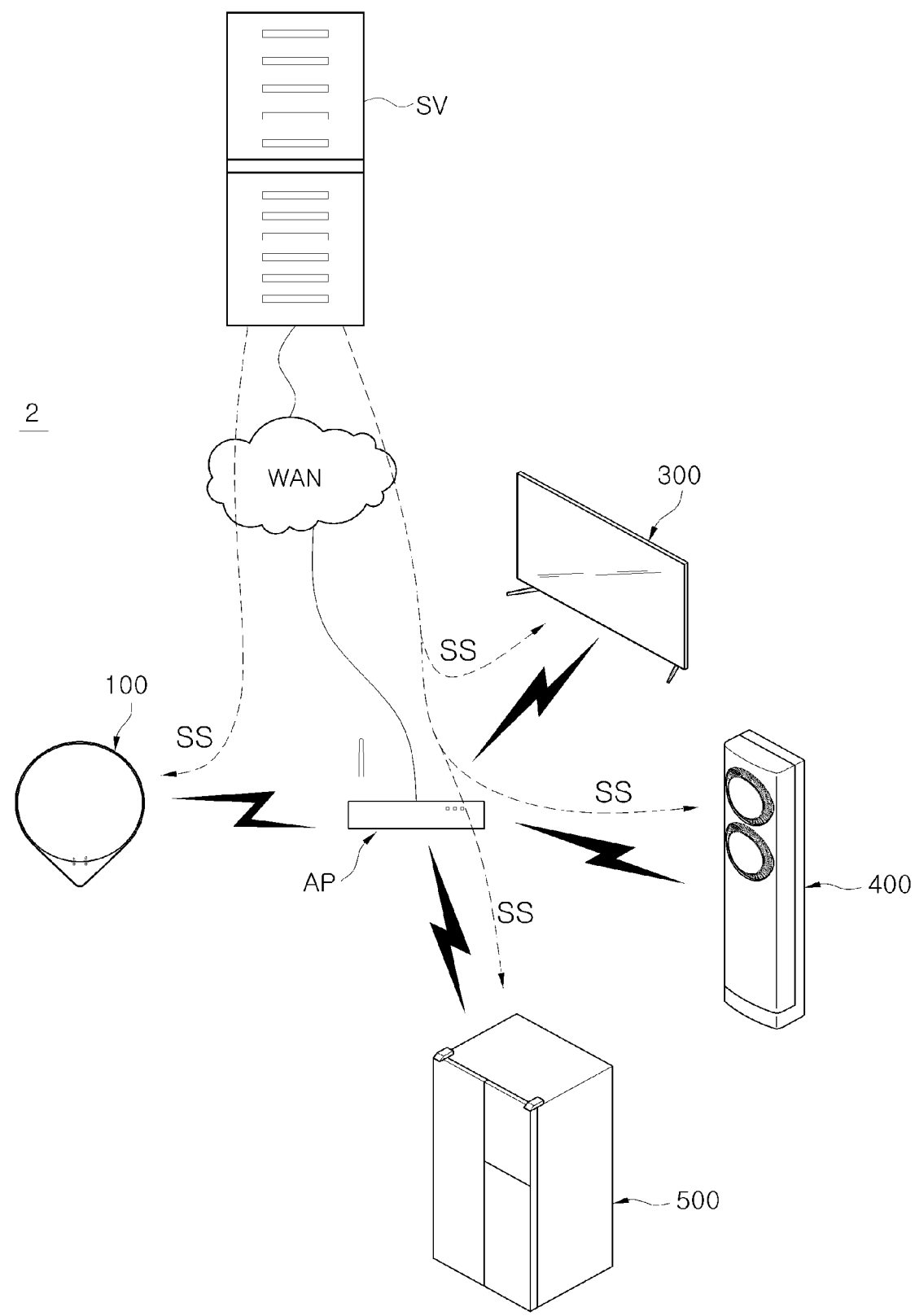
[Fig. 26]

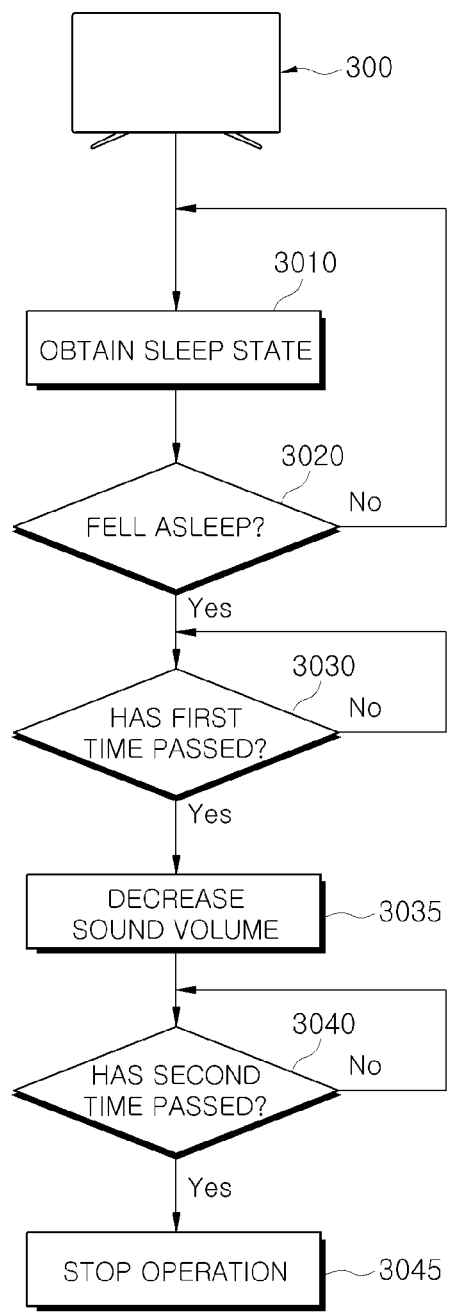

[Fig. 28]
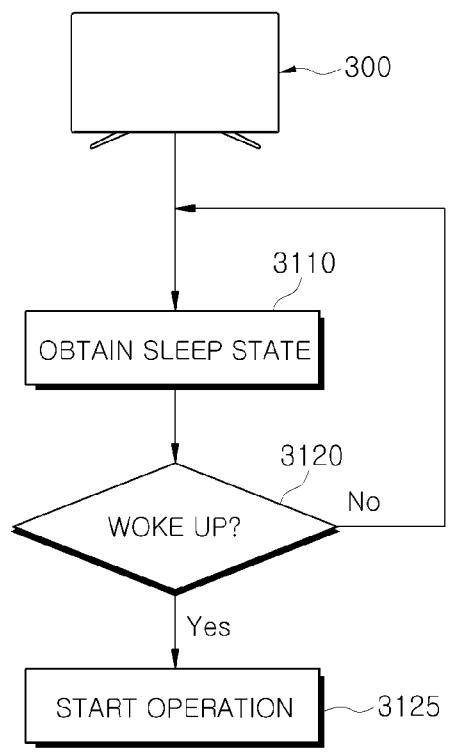

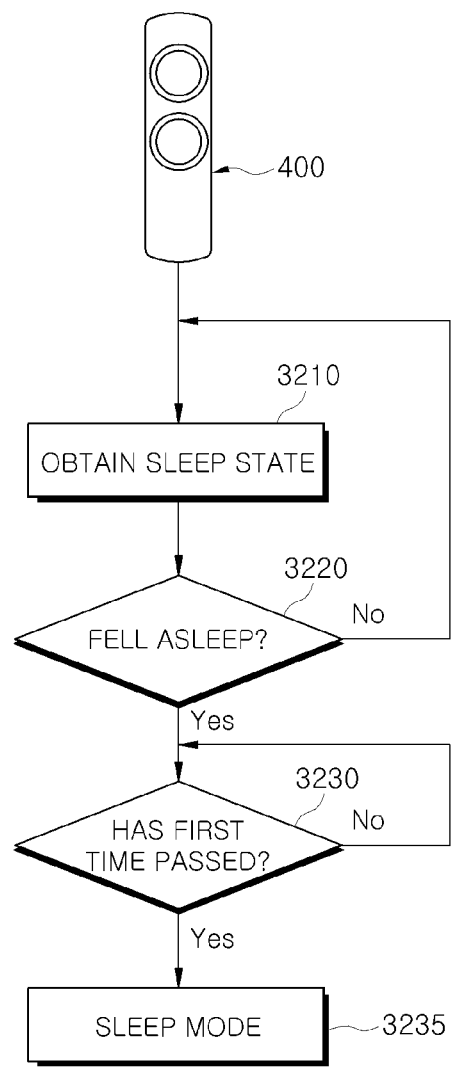

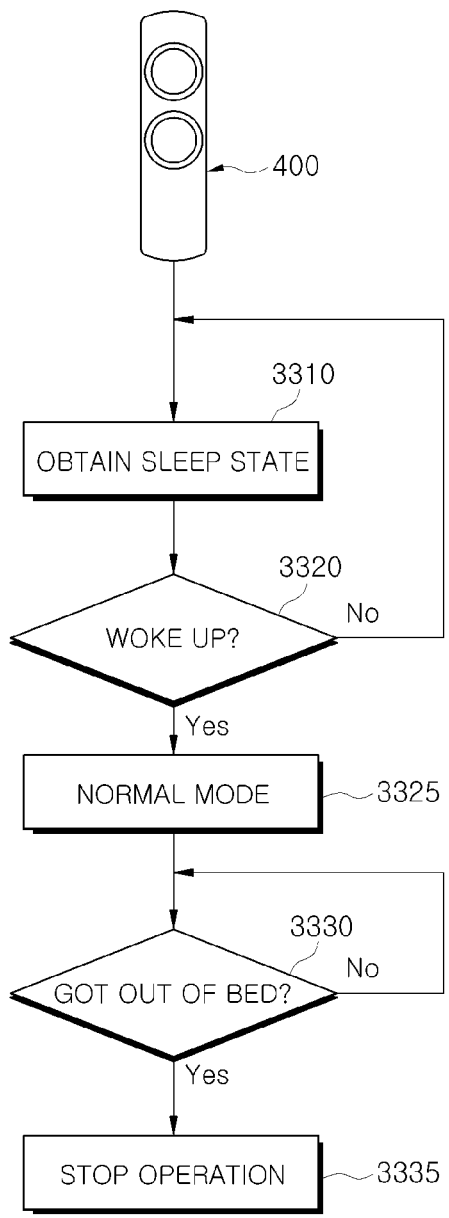
[Fig. 30]

USER TERMINAL AND SLEEP MANAGEMENT METHOD

CROSS-REFERENCE TO RELATED APPLICATIONS AND CLAIM OF PRIORITY

The present application is a 371 National Stage of International Application No. PCT/KR2016/009594 filed on Aug. 29, 2016, which claims the benefit of Korean Patent Application No. 10-2015-0124571 filed on Sep. 3, 2015, the contents of which are incorporated herein by reference.

TECHNICAL FIELD

The present disclosure relates to a user terminal and a sleep management method, and more particularly, to a user terminal and a sleep management method that obtains sleep information of a user in a non-contact manner.

BACKGROUND

Generally, home network systems detect a state or operation of a user and control operation of various electronic devices depending on the state or operation of the user.

To this end, electronic devices of home network systems generally include various sensors.

For example, some electronic devices may obtain a facial image of a user using a camera, process the user's facial image, and estimate an emotion of the user.

Also, other electronic devices may obtain movement of a user and then operate depending on the user's movement.

In particular, recently, research is being actively conducted on sensor technology for detecting whether a user is sleeping.

SUMMARY

An aspect of the present disclosure is directed to providing a user terminal and a sleep management method that are capable of determining a sleep state of a user.

Another aspect of the present disclosure is directed to providing a user terminal and a sleep management method that are capable of providing sleep information of a user.

Another aspect of the present disclosure is directed to providing a user terminal and a sleep management method that are capable of controlling operation of a home appliance according to a sleep state of a user.

In accordance with one aspect of the present disclosure, a sleep management method includes obtaining sleep data of a user, obtaining a sleep state of the user on the basis of the sleep data, and controlling at least one home appliance on the basis of the sleep state of the user, and the sleep data includes signals corresponding to a heart rate, respiration rate, and movement of the user detected by a piezoelectric sensor.

The obtaining of a sleep state of the user on the basis of the sleep data may include obtaining a first signal corresponding to the user's heart rate, a second signal corresponding to the user's respiration rate, and a third signal corresponding to the user's movement, from the sleep data, and identifying the sleep state of the user on the basis of the obtained first signal, second signal, and third signal.

The obtaining of a sleep state of the user on the basis of the sleep data may include transmitting the sleep data to a sleep management server, and receiving the sleep state of the user from the sleep management server.

The controlling of at least one home appliance on the basis of the sleep state of the user may include providing a graphic user interface for controlling operation of the at least one home appliance to the user, receiving a user input from the user through the graphic user interface, and storing setting information for controlling the operation of the at least one home appliance according to the user input.

The providing of a graphic user interface may include displaying at least one of a total sleep time, a time it takes the user to fall asleep, the number of times the user wakes up while sleeping, sleep efficiency, a deep sleep time, and a rapid eye movement sleep time of the user.

The providing of a graphic user interface may include displaying a sleep environment setting screen for setting an indoor temperature during the user's sleep.

The controlling of at least one home appliance may include transmitting an indoor temperature set through the sleep environment setting screen to the home appliance and switching an operation mode of the at least one home appliance in response to detecting the user's sleep.

The providing of a graphic user interface may include displaying a sleep environment setting screen for setting a sleep induction temperature for inducing the user's sleep, a sleep maintenance temperature for maintaining the user's sleep, and a sleep stop temperature for stopping the user's sleep.

The controlling of at least one home appliance may include transmitting the sleep induction temperature, the sleep maintenance temperature, and the sleep stop temperature set through the sleep environment setting screen to the home appliance and switching an operation mode of the at least one home appliance in response to detecting the user's sleep.

The providing of a graphic user interface may include displaying a sleep environment setting screen for selecting whether to turn off the at least one home appliance while the user sleeps.

The controlling of at least one home appliance may include transmitting an operation stop command for turning off the at least one home appliance to the at least one home appliance in response to detecting the user's sleep.

In accordance with one aspect of the present disclosure, a user terminal includes a communicator configured to communicate with a sleep data acquisition apparatus and at least one home appliance, and a controller configured to, in response to receiving sleep data from the sleep data acquisition apparatus through the communicator, obtain a sleep state of a user on the basis of the sleep data and transmit a control signal based on the sleep state of the user to the at least one home appliance through the communicator, and the sleep data includes signals corresponding to a heart rate, respiration rate, and movement of the user detected by a piezoelectric sensor.

The controller may obtain a first signal corresponding to the user's heart rate, a second signal corresponding to the user's respiration rate, and a third signal corresponding to the user's movement from the sleep data, and identify the sleep state of the user on the basis of the obtained first signal, second signal, and third signal.

The controller may transmit the sleep data to a sleep management server by using the communicator, and receive the sleep state of the user from the sleep management server by using the communicator.

The user terminal may further include a display configured to display a graphic user interface for controlling operation of the at least one home appliance, and the controller may receive a user input from the user through the graphic user interface and store setting information for controlling the operation of the at least one home appliance according to the user input.

The graphic user interface may include a sleep information display screen for displaying at least one of a total sleep time, a time it takes the user to fall asleep, the number of times the user wakes up while sleeping, sleep efficiency, a deep sleep time, and a rapid eye movement sleep time of the user.

The graphic user interface may include a sleep environment setting screen for setting an indoor temperature during the user's sleep.

In response to detecting the user's sleep, the controller may transmit the indoor temperature set through the sleep environment setting screen to the home appliance by using the communicator, and switch an operation mode of the at least one home appliance.

The graphic user interface may include a sleep environment setting screen for setting a sleep induction temperature for inducing the user's sleep, a sleep maintenance temperature for maintaining the user's sleep, and a sleep stop temperature for stopping the user's sleep.

In response to detecting the user's sleep, the controller may transmit the sleep induction temperature, the sleep maintenance temperature, and the sleep stop temperature set through the sleep environment setting screen to the home appliance, and switch an operation mode of the at least one home appliance.

The graphic user interface includes a sleep environment setting screen for selecting whether to turn off the at least one home appliance while the user sleeps.

In response to detecting the user's sleep, the controller transmits an operation stop command for turning off the at least one home appliance to the at least one home appliance.

According to an aspect of the present disclosure, it is possible to provide a user terminal and a sleep management method that are capable of determining a sleep state of a user.

According to another aspect of the present disclosure, it is possible to provide a user terminal and a sleep management method that are capable of providing sleep information of a user to the user.

According to another aspect of the present disclosure, it is possible to provide a user terminal and a sleep management method that are capable of controlling operation of a home appliance according to a sleep state of a user.

BRIEF DESCRIPTION OF THE DRAWINGS

FIG. 5 shows a configuration of a sleep data acquisition apparatus included in a sleep management system according to an embodiment;

FIG. 6 shows a configuration of a user terminal included in a sleep management system according to an embodiment;

FIG. 7 shows an example of communication between a sleep management system and home appliances according to an embodiment;

FIG. 8 shows another example of communication between a sleep management system and home appliances according to an embodiment;

FIG. 9 shows an example of interoperation between a sleep management system and an image display apparatus according to an embodiment;

FIG. 10 shows operation of an image display apparatus during the interoperation shown in FIG. 9;

FIG. 11 shows another example of interoperation between a sleep management system and an image display apparatus according to an embodiment;

FIG. 12 shows operation of an image display apparatus during the interoperation shown in FIG. 11;

FIG. 13 shows an example of interoperation between a sleep management system and an air conditioner according to an embodiment;

FIG. 14 shows an example of operation of the air conditioner during the interoperation shown in FIG. 13;

FIG. 15 shows an example of operation of the air conditioner in a sleep mode;

FIG. 16 shows another example of interoperation between a sleep management system and an air conditioner according to an embodiment;

FIG. 17 shows operation of the air conditioner during the interoperation shown in FIG. 16;

FIG. 18 shows an example of a sleep information display screen displayed on a user terminal according to an embodiment;

FIG. 19 shows an example of a home appliance setting screen displayed on a user terminal according to an embodiment;

FIG. 20 shows an example of an air conditioner setting screen displayed on a user terminal according to an embodiment;

FIG. 21 shows an example of an image display apparatus setting screen display on a user terminal according to an embodiment;

FIG. 22 shows an example of a sleep environment setting screen displayed on a user terminal according to an embodiment;

FIG. 23 shows an example of an indoor temperature setting screen displayed on a user terminal according to an embodiment;

FIG. 24 shows a change in indoor temperature caused by the indoor temperature setting screen shown in FIG. 23;

FIG. 25 shows an example of communication between a sleep management system and home appliances according to another embodiment;

FIG. 26 shows another example of communication between a sleep management system and home appliances according to another embodiment;

FIG. 27 shows an example of operation of an image display apparatus included in a sleep management system according to another embodiment;

FIG. 28 shows another example of operation of an image display apparatus included in a sleep management system according to another embodiment;

FIG. 29 shows an example of operation of an air conditioner included in a sleep management system according to another embodiment; and FIG. 30 shows another example of operation of an air conditioner included in a sleep management system according to another embodiment.

DETAILED DESCRIPTION

Figure 1:
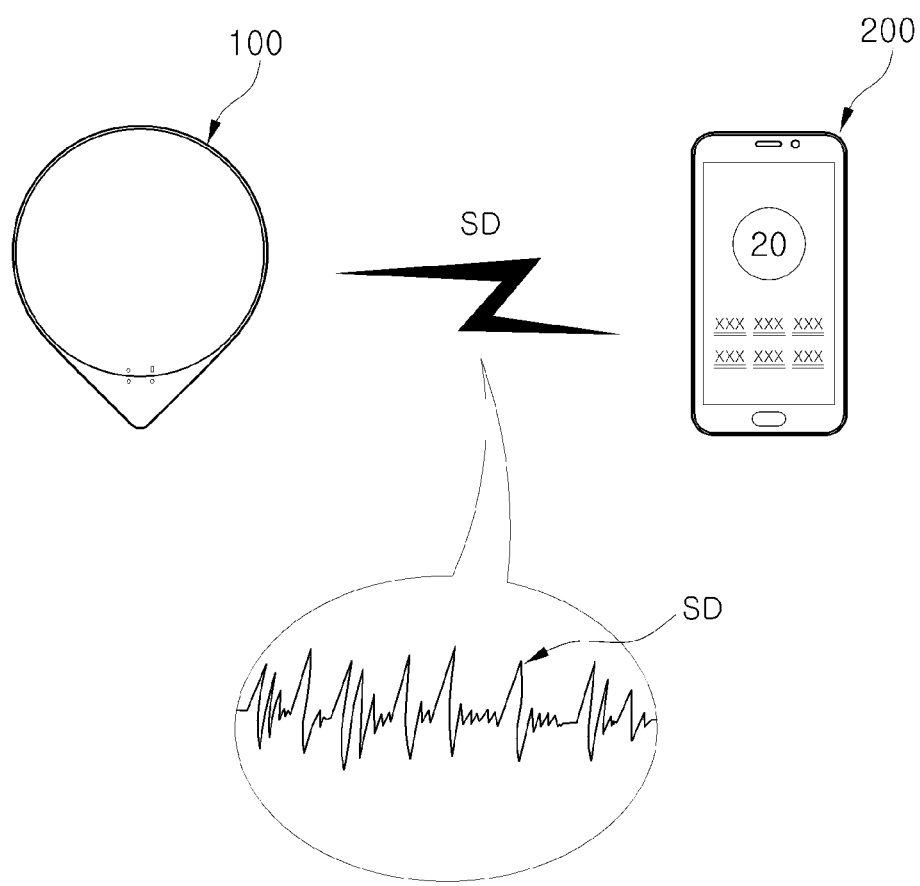
FIG. 1 shows an example of a configuration of a sleep management system according to an embodiment.

The configurations shown in the embodiments and drawings described herein are merely examples of preferred embodiments of the present disclosure, and there may be various modifications at the time of filing of the present application that replace the embodiments and drawings.

The terminology used herein is for the purpose of describing particular embodiments only and is not intended to limit the scope of the present disclosure.

Specifically, the singular forms "a," "an," and "the" include the plural forms as well, unless the context clearly dictates otherwise.

Also, the terms "comprises," "includes," or "has," when used herein, should be understood as specifying the presence of stated features, integers, steps, operations, elements, components, or combinations thereof and not precluding the presence or addition of one or more other features, integers, steps, operations, elements, components, or combinations thereof.

In addition, terms including ordinals such as "first," "second," and the like used in the present specification may be used to describe various elements, but these elements are not limited by the terms. These terms are used to only distinguish one element from another element.

Also, terms such as "unit," "-er," "-or," "block," "member," "module," and the like used in the present specification may represent a unit which processes at least one function or operation. For example, the terms may represent hardware such as a field-programmable gate array (FPGA) or an application specific integrated circuit (ASIC), software stored in a memory, or one or more processes processed by a processor.

Hereinafter, an embodiment of the present disclosure will be described in detail with reference to the accompanying drawings. The same reference numeral or symbol shown in the accompanying drawings may represent a part or an element for performing substantially the same function.

Figure 2:
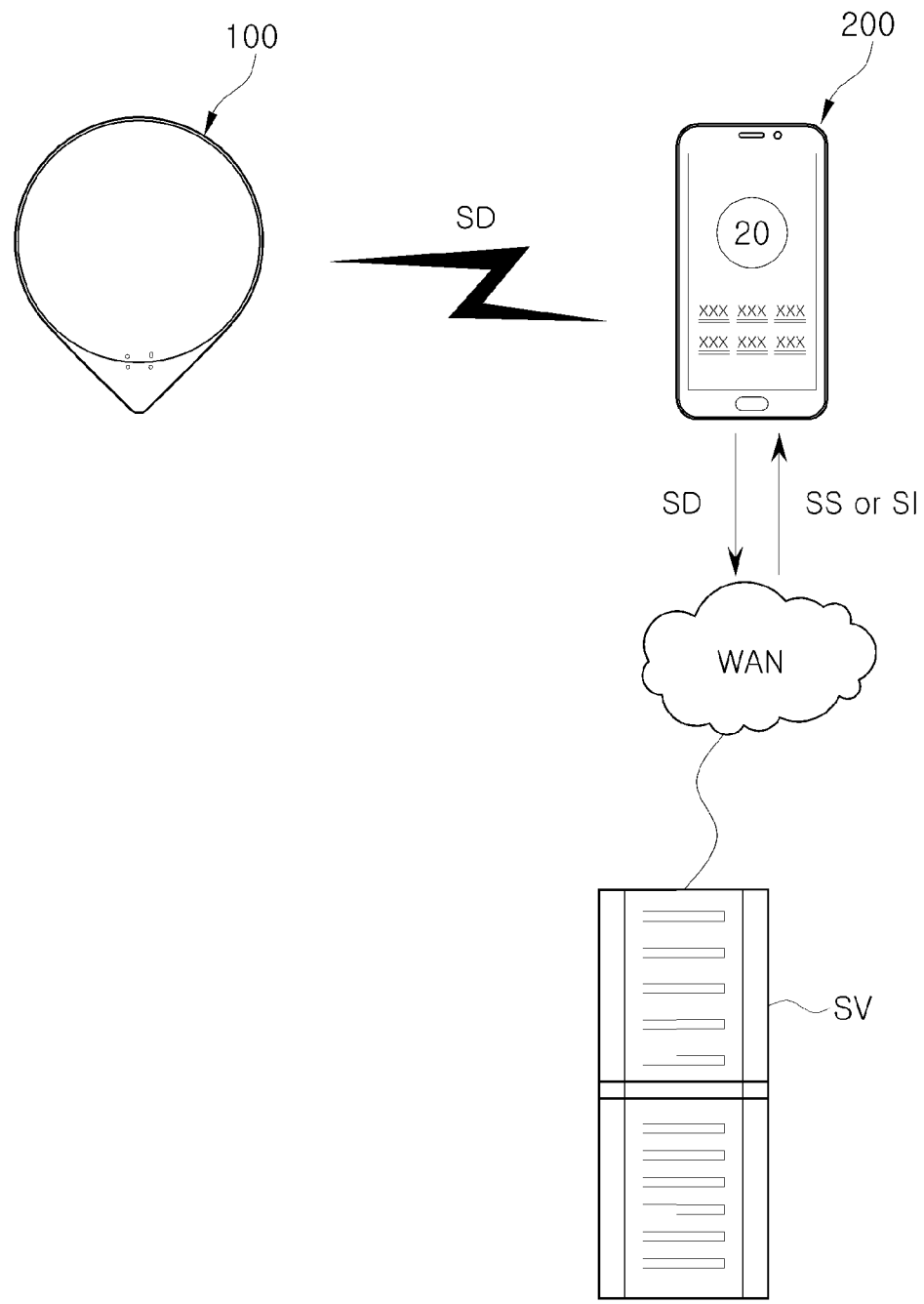
FIG. 2 shows another example of a configuration of a sleep management system according to an embodiment.

FIG. 1 shows an example of a configuration of a sleep management system according to an embodiment, and FIG. 2 shows another example of a configuration of a sleep management system according to an embodiment.

As shown in FIG. 1, a sleep management system 1 according to an embodiment may include a sleep data acquisition apparatus 100 configured to obtain sleep-related data SD (hereinafter referred to as sleep data) of a user, and a user terminal 200 configured to obtain sleep-related information (hereinafter referred to as sleep information) of the user on the basis of the sleep data SD. In this case, the sleep information may include sleep time information related to a sleep time of a user U, and sleep summary information to be displayed to the user U.

The sleep data acquisition apparatus 100 may collect the sleep data SD of the user while the user is sleeping, falling asleep, or waking up. Also, the sleep data acquisition apparatus 100 may transmit the sleep data SD of the user to the user terminal 200.

In detail, the sleep data acquisition apparatus 100 may detect a heart rate, respiration rate, and movement of the user and generate sleep data SD corresponding to the user's heart rate, respiration rate, and movement. For example, the sleep data acquisition apparatus 100 may detect a vibration caused by the user's heart rate, respiration rate, and movement and generate sleep data SD corresponding to the detected vibration.

Also, the sleep data acquisition apparatus 100 may transmit pieces of sleep data SD generated every predetermined time interval to the user terminal 200 in a wireless manner.

The user terminal 200 may receive the sleep data SD of the user from the sleep data acquisition apparatus 100, and may obtain a sleep state SS of the user or sleep information SI of the user on the basis of the received sleep data SD.

For example, the user terminal 200 may obtain the sleep state SS of the user U. In detail, the user terminal 200 may determine whether the user U is lying on a bed B, whether the user U is sleeping, in which sleep stage the user U is, whether the user U wakes up briefly while sleeping, whether the user U is falling asleep again, whether the user U completely wakes up, whether the user U gets out of the bed B, and the like.

Also, the user terminal 200 may obtain sleep time information such as a time at which the user U lies on the bed B, a time at which the user U falls asleep, a time at which the sleep stage of the user U changes, a time at which the user U wakes up briefly while sleeping, a time at which the user U falls asleep again, a time at which the user U wakes up, and a time at which the user U gets out of the bed B on the basis of the sleep state SS of the user U.

Also, the user terminal 200 may process the sleep time information of the user U, generate sleep summary information, and display the sleep summary information to the user U. For example, the user terminal 200 may display a total sleep time, a time it takes the user to fall asleep, the number of times the user wakes up while sleeping, sleep efficiency, a deep sleep time, a rapid eye movement (REM) sleep time, or the like of the user on the basis of the sleep data SD of the user.

However, the configuration of the sleep management system 1 is not limited to that shown in FIG. 1.

For example, as shown in FIG. 2, the sleep management system 1 may further include a sleep management server SV in addition to the sleep data acquisition apparatus 100 and the user terminal 200.

The sleep management server SV may receive the sleep data SD from the user terminal 200, process the received sleep data SD, and generate the sleep state SS or the sleep information SI of the user U. Also, the sleep management server SV may transmit the sleep state SS or the sleep information SI of the user U to the user terminal 200.

In other words, when the sleep data SD is obtained from the sleep data acquisition apparatus 100, the user terminal 200 may transmit the obtained sleep data SD to the sleep management server SV over a wide area network (WAN) and receive the sleep state SS or the sleep information SI of the user U from the sleep management server SV. Also, when the sleep state SS of the user U is received from the sleep management server SV, the user terminal 200 may generate the sleep information SI of the user U on the basis of the sleep state SS of the user U.

In particular, the sleep management server SV may obtain sleep data of a plurality of users from a plurality of user terminals, process the sleep data, and generate sleep information of the plurality of users. In this case, the sleep management server SV may manage the sleep information of the plurality of users on a user basis.

In addition, the sleep management server SV may manage the sleep information SI of the plurality of users on a group basis, wherein the groups are set by the users. For example, when the plurality of users are set as family members, the sleep management server SV may transmit sleep information of the family members (the plurality of users) to user terminals of the family members so that the family members can share the sleep information.

Operation of the sleep management system 1 will be described in detail below with reference to the following example.

Figure 3:
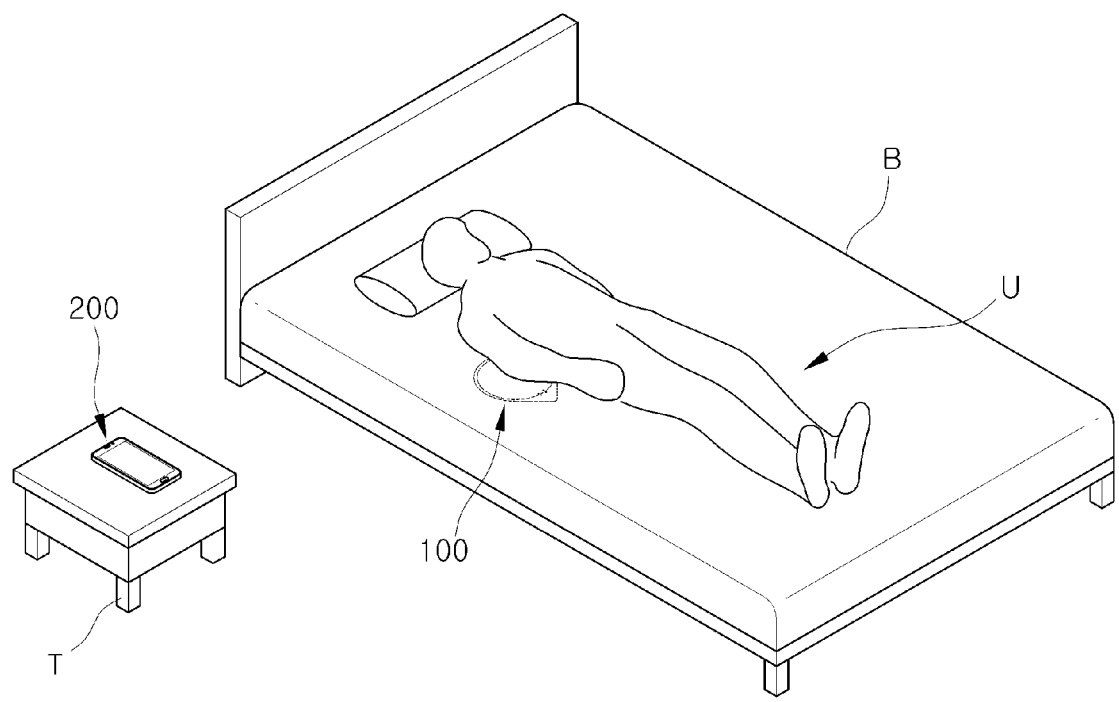
FIG. 3 shows an example of operation of a sleep management system according to an embodiment.
Figure 4:
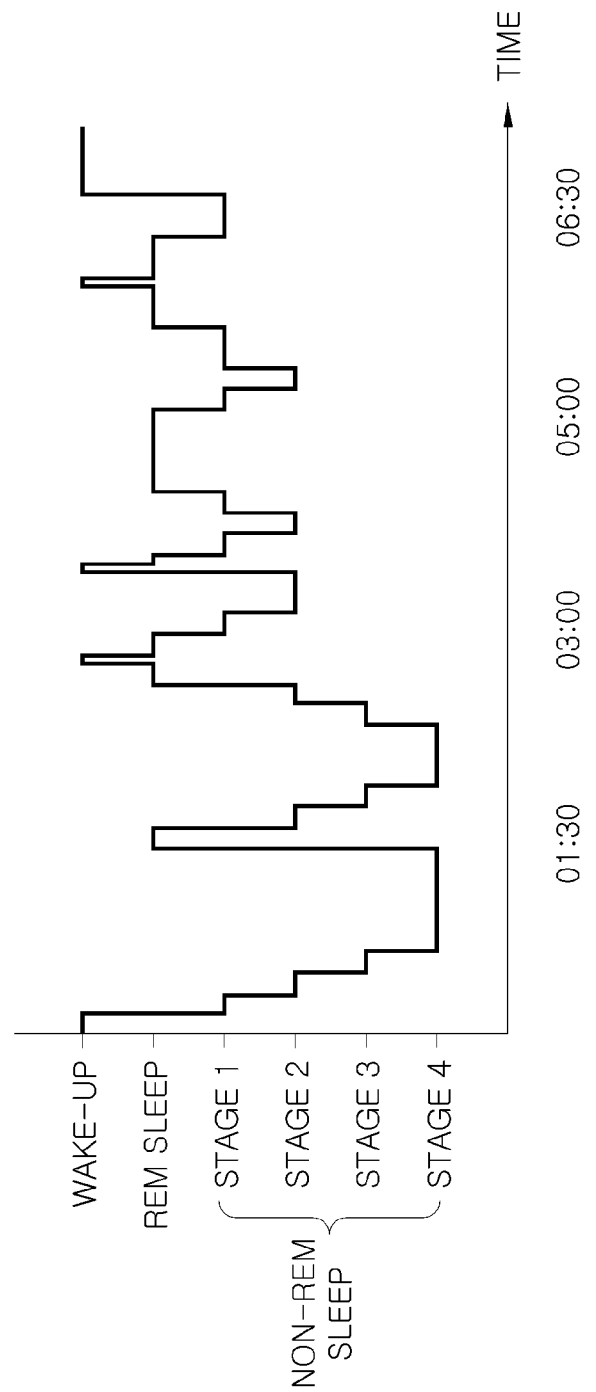
FIG. 4 shows an example of a user's sleep cycle shown in FIG. 3.

FIG. 3 shows an example of operation of a sleep management system according to an embodiment, and FIG. 4 shows an example of a user's sleep cycle shown in FIG. 3.

As shown in FIG. 3, the sleep data acquisition apparatus 100 may be placed near a user U who is lying on a bed B. For example, as shown in FIG. 3, the sleep data acquisition apparatus 100 may be placed under the bed B of the user U. However, the placement of the sleep data acquisition apparatus 100 is not limited to that shown in FIG. 3, and the sleep data acquisition apparatus 100 may be placed wherever a heart rate, respiration rate, and movement of the user U can be detected.

Also, the user terminal 200 may be placed near the sleep data acquisition apparatus 100. For example, as shown in FIG. 3, the user terminal 200 may be placed on a table T provided near the bed B of the user U. However, the placement of the user terminal 200 is not limited to that shown in FIG. 3, and the user terminal 200 may be placed wherever the sleep data SD can be received from the sleep data acquisition apparatus 100.

As shown in FIG. 3, when the user U lies on the bed B, the sleep data acquisition apparatus 100 may detect a heart rate, respiration rate, and movement of the user U who is lying on the bed B and transmit sleep data SD corresponding to the user U's heart rate, respiration rate, and movement to the user terminal 200. Also, the user terminal 200 may determine a time at which the user U lies on the bed B on the basis of the sleep data SD or by using the sleep management server SV.

For example, the sleep data acquisition apparatus 100 can detect an amount of vibration less than a reference value, which is caused in daily life of the user U, before the user U lies on the bed B. However, the sleep data acquisition apparatus 100 may interpret the amount of vibration less than the reference value as meaningless noise and not transmit data corresponding to the amount of vibration less than the reference value to the user terminal 200. As a result, the user terminal 200 may not receive sleep data from the sleep data acquisition apparatus 100 before the user U lies on the bed B.

On the other hand, the user terminal 200 may detect an amount of vibration greater than or equal to the reference value when the user U lies on the bed B. The sleep data acquisition apparatus 100 may transmit sleep data corresponding to the amount of vibration greater than or equal to the reference value to the user terminal 200.

When the sleep data is received from the sleep data acquisition apparatus 100, the user terminal 200 or the sleep management server SV may determine that the user U is lying on the bed B and determine a start time of the reception of the sleep data as a time at which the user U lies on the bed B.

Also, when the user U falls asleep, the sleep data acquisition apparatus 100 may detect a heart rate, respiration rate, and movement of the user U who is sleeping and transmit sleep data SD corresponding to the user U's heart rate, respiration rate, and movement to the user terminal 200. Also, the user terminal 200 may determine a time at which the user U falls asleep on the basis of the sleep data SD or by using the sleep management server SV.

In detail, the user U may not fall asleep as soon as the user U lies on the bed B and may not fall asleep for a short period of several minutes or for several hours. Accordingly, the time at which the user U lies on the bed B may be different from the time at which the user falls asleep.

Also, the user U has a different heart rate, respiration rate, and movement when he or she is awake than when he or she is asleep. In detail, it is well known that a person has a decreased heart rate and respiration rate while sleeping.

Accordingly, when the sleep data is received from the sleep data acquisition apparatus 100, the user terminal 200 or the sleep management server SV may determine whether the user U is awake or asleep on the basis of the user U's heart rate, respiration rate, and movement and determine the time at which the user falls asleep on the basis of a result of the determination of whether the user U is awake or asleep.

Also, while the user U is sleeping, the sleep data acquisition apparatus 100 may detect the user U's heart rate, respiration rate, and movement every predetermined time interval and transmit sleep data SD corresponding to the user U's heart rate, respiration rate, and movement to the user terminal 200.

On the basis of the sleep data SD of the user U during sleep, the user terminal 200 or the sleep management server SV may determine a sleep stage of the user U and determine whether the user U consciously or unconsciously wakes up.

It is well known that a person does not suddenly fall asleep, maintain deep sleep, and then suddenly wake up, but that human sleep includes certain stages and cycles. For example, as shown in FIG. 4, human sleep gradually proceeds to a deep sleep stage after falling sleep. Subsequently, human sleep repeatedly alternates between a light sleep stage and the deep sleep stage.

As is already well known, human sleep may be largely divided into REM sleep and non-REM sleep, and non-REM sleep may be divided into a total of four stages.

It is well known that REM sleep makes up about 20% to 25% of the entire sleep, and during REM sleep, a characteristic electroencephalogram (EEG) exists, muscle tension is reduced to the lowest level and characteristic REM is observed.

In particular, a significant change occurs in heart rate and respiration rate during REM sleep.

Also, non-REM sleep may be divided into a first stage, a second stage, a third stage, and a fourth stage, as described above. Sleep in the third stage and the fourth stage is typically referred to as deep sleep, and sleep in the first stage and the second stage is typically referred to as light sleep. Here, it is known that the deep sleep makes up about 15 to 20% of the entire sleep.

During non-REM sleep, muscle tension is reduced and human movement is also reduced.

In particular, it is known that a heart rate and a respiration rate during non-REM sleep are decreased further than during waking and are relatively regular.

As described above, human sleep exhibits a characteristic heart rate, respiration rate, and movement in each of the stages. Thus, the user terminal 200 or the sleep management server SV may determine a sleep stage of the user U on the basis of the sleep data SD indicating the user U's heart rate, respiration rate, and movement during sleep.

For example, the user terminal 200 or the sleep management server SV may determine whether the sleep of the user U enters or exits a REM sleep stage, and may determine and/or store a time at which the REM sleep stage is entered and a time at which the REM sleep stage is exited.

As another example, the user terminal 200 or the sleep management server SV may determine whether the sleep of the user U enters or exits deep sleep stages (the third and fourth stages) of non-REM sleep, and may determine and/or store a time at which the deep sleep stage is entered and a time at which the deep sleep stage is exited.

Also, it is known that a sleeping person consciously or unconsciously wakes up. For example, as shown in FIG. 4, a person enters a waking stage during REM sleep. Also, in the waking stage, a person may consciously or unconsciously wake up, and, while waking, his or her heart rate and respiration rate increase, and his or her movement becomes active.

Accordingly, the user terminal 200 or the sleep management server SV may determine whether the user U wakes from sleep on the basis of the sleep data SD indicating the user U's heart rate, respiration rate, and movement during sleep.

For example, the user terminal 200 or the sleep management server SV may determine whether the user U wakes from the sleep, and may determine and/or store a time at which the user U wakes up. Also, when the user U falls asleep again within a reference time (e.g., 30 minutes) after waking up, the user terminal 200 or the sleep management server SV may determine that the user U continues to sleep, and may determine and/or store a time at which the user U falls asleep again.

Also, when sleep is completed, the user U may wake up and then get out of the bed B. When the user U wakes up and gets out of the bed B, the user terminal 200 or the sleep management server SV may determine whether the user U wakes up and whether the user U gets out of the bed B on the basis of the sleep data SD received from the sleep data acquisition apparatus 100. Also, the user terminal 200 or the sleep management server SV may determine and/or store a time at which the user U wakes up and a time at which the user U gets out of the bed B.

As described above, the user terminal 200 or the sleep management server SV may obtain the sleep information SI of the user U on the basis of the sleep data SD. In detail, the user terminal 200 or the sleep management server SV may obtain sleep time information such as a time at which the user U lies on the bed B, a time at which the user U falls asleep, a time at which the sleep stage of the user U changes, a time at which the user U wakes up briefly while sleeping, a time at which the user U falls asleep again, a time at which the user U wakes up, and a time at which the user U gets out of the bed B.

Also, the user terminal 200 or the sleep management server SV may generate sleep summary information of the user U on the basis of the sleep time information of the user U. For example, the user terminal 200 or the sleep management server SV may obtain sleep summary information such as a total sleep time, a time it takes the user to fall asleep, the number of times the user wakes up while sleeping, sleep efficiency, a deep sleep time, and a REM sleep time on the basis of the sleep time information of the user U.

Also, the user terminal 200 may display the sleep summary information to the user according to input of the user.

Configurations of the sleep data acquisition apparatus 100 and the user terminal 200 included in the sleep management system 1 will be described below.

FIG. 5 shows a configuration of a sleep data acquisition apparatus included in a sleep management system according to an embodiment.

As shown in FIG. 5, the sleep data acquisition apparatus 100 may include a sleep sensor 120, a sensor communicator 130, and a sensor controller 110.

The sleep sensor 120 may detect a heart rate, a respiration rate, and a movement of a user who is lying on a bed and output an electrical signal corresponding to the detected heart rate, respiration rate, and movement of the user to the sensor controller 110.

For example, the sleep sensor 120 may include a piezoelectric sensor 121 configured to detect pressure caused by the heart rate, respiration rate, and movement of the user and output an electrical signal corresponding to the detected pressure. The piezoelectric sensor 121 uses a piezoelectric effect in which electric polarization occurs on a surface of a crystal when a force is applied to the crystal. The piezoelectric sensor 121 generates an alternating current (AC) voltage when pressure is applied thereto, and generates a vibration when the AC voltage is applied thereto.

In detail, when pressure is applied to the piezoelectric sensor 121 by the heart rate, respiration rate, and movement of the user, the piezoelectric sensor 121 may output an electrical signal corresponding to the pressure applied thereto.

As another example, the sleep sensor 120 may include an acceleration sensor 123 configured to detect a vibration caused by the heart rate, respiration rate, and movement of the user and output an electrical signal corresponding to the detected vibration.

The acceleration sensor 123 is a sensor configured to measure a change in speed per unit time. When the acceleration sensor 123 is moved or vibrated by the heart rate, respiration rate, and movement of the user, the acceleration sensor 123 may output an electrical signal corresponding to the movement or vibration.

However, the sleep sensor 120 does not have to include both of the piezoelectric sensor 121 and the acceleration sensor 123. Depending on a designer's selection, the sleep sensor 120 may include either the piezoelectric sensor 121 or the acceleration sensor 123.

The sensor communicator 130 may include a short-range communication module 131 configured to transmit and/or receive data to and/or from the user terminal 200.

The short-range communication module 131 may communicate with a communication partner through various communication schemes. For example, the short-range communication module 131 may communicate with a communication partner through a WiFi communication scheme (IEEE 802.11), a Bluetooth communication scheme (IEEE 802.15.1), a Zigbee communication scheme (IEEE 802.15.4), or the like.

However, the short-range communication module 131 does not employ all of the WiFi communication scheme, the Bluetooth communication scheme, and the Zigbee communication scheme, and may employ at least one of the WiFi communication scheme, the Bluetooth communication scheme, and the Zigbee communication scheme.

The sensor controller 110 may include a memory 113 configured to store and/or recall programs and data, and a processor 111 configured to process the data according to the programs stored in the memory 113 and control the sleep sensor 120 and the sensor communicator 130.

The memory 113 may store a control program and control data for controlling operation of the sleep data acquisition apparatus 100, or may recall sleep data SD obtained through the sleep sensor 120.

The memory 113 may include a volatile memory such as a static random access memory (S-RAM) and a dynamic RAM (D-RAM) and a non-volatile memory such as a read-only memory (ROM), an erasable programmable ROM (EPROM), an electrically erasable programmable ROM (EEPROM), and a flash memory.

The volatile memory, which is a memory that loses data recalled therein when power is cut off, may temporarily recall programs and data. For example, the volatile memory may recall a control program and control data or recall the sleep data SD obtained by the sleep sensor 120.

The non-volatile memory, which is a memory that maintains data stored therein even though power is cut off, may semi-permanently store programs and data. For example, the non-volatile memory may store a control program and control data for controlling operation of the sleep data acquisition apparatus 100.

The processor 111 may process the sleep data SD input from the sleep sensor 120 according to the control program and control data stored in the memory 113 and transmit the sleep data to the user terminal 200 through the sensor communicator 130.

For example, the processor 111 may obtain an electrical signal output by the sleep sensor 120 every predetermined time interval and generate the sleep data SD by digitalizing the obtained electrical signal. Also, the processor 111 may output the sleep data SD and a control signal to the sensor communicator 130 so that the sensor communicator 130 can transmit the sleep data SD to the user terminal 200.

As described above, the sensor controller 110 may control operation of the sleep sensor 120 and the sensor communicator 130 included in the sleep data acquisition apparatus 100. An operation of the sleep data acquisition apparatus 100, which will be described below, may be interpreted as being controlled by the sensor controller 110.

FIG. 6 shows a configuration of a user terminal included in a sleep management system according to an embodiment.

As shown in FIG. 6, the user terminal 200 may include a user input/output unit 220, a terminal communicator 230, a terminal storage 240, and a terminal controller 210.

The user input/output unit 220 may receive a user input from a user and output information corresponding to the user input.

For example, the user input/output unit 220 may include a touch screen module 221 configured to receive a touch input from a user and display information corresponding to the received touch input, a button module 223 configured to receive a predetermined user input from the user, a microphone 225 configured to receive a voice input from the user, and a speaker 227 configured to output sounds.

The touch screen module 221 may receive a touch input from a user and display image information corresponding to the received touch input.

In detail, the touch screen module 221 may receive at least one touch or a continuous touch movement through the user's body (e.g., his or her finger) or a touchable input means (e.g., a stylus pen).

The touch screen module 221 may convert the touch input of the user into a digital signal corresponding to the touch input (e.g., an x coordinate and a y coordinate) and output the digital signal to the terminal controller 210.

The touch screen module 221 may be implemented as a resistive-type module, a capacitive-type module, an infrared-type module, or an acoustic-wave-type module.

The button module 223 may be provided on a front surface, a side surface, or a rear surface of a housing of the user terminal 200, and may include a plurality of buttons capable of receiving a predetermined user input. The button module 223 may include at least one of a power/lock button, a volume button, a menu button, a home button, and a return button.

The terminal communicator 230 may transmit and/or receive data to and/or from the sleep data acquisition apparatus 100 and the sleep management server SV, which have been described above. In addition, the terminal communicator 230 may transmit and/or receive data to and/or from other user terminals.

The terminal communicator 230 may include a short-range communication module 231 configured to transmit and/or receive data to and/or from a communication partner at a location that is relatively near the communication partner, and a mobile communication module 233 configured to transmit and/or receive data to and/or from a communication partner regardless of a distance from the communication partner.

The short-range communication module 231 may communicate with a communication partner through various communication schemes. For example, the short-range communication module 231 may communicate with a communication partner through a WiFi communication scheme (IEEE 802.11), a Bluetooth communication scheme (IEEE 802.15.1), a Zigbee communication scheme (IEEE 802.15.4), or the like However, the short-range communication module 231 does not employ all of the WiFi communication scheme, the Bluetooth communication scheme, and the Zigbee communication scheme, and may employ at least one of the WiFi communication scheme, the Bluetooth communication scheme, and the Zigbee communication scheme.

The mobile communication module 233 may communicate with a communication partner through various communication schemes. For example, the mobile communication module 233 may communicate with the communication partner by using a second generation communication scheme such as time division multiple access (TDMA) and code division multiple access (CDMA), a third generation communication scheme such as wideband code division multiple access (WCDMA), code division multiple access 2000 (CDMA2000), wireless broadband (Wibro), and world interoperability for microwave access (WiMAX), a fourth generation communication scheme such as long term evolution (LTE) and wireless broadband evolution, or the like.

Various application programs and data for performing various functions may be stored in the terminal storage 240 according to a user input received through the user input/output unit 220. For example, an operating system (OS) program for managing configurations and resources (software and hardware) included in the user terminal 200, a video playback program for playing a video and displaying a picture, a word processor program for creating and editing a document, a browser for accessing a WAN such as the Internet, and the like may be stored in the terminal storage 240.

The terminal storage 240 may include a non-volatile memory in which no program or data is lost even when power is cut off. For example, the terminal storage 240 may include a flash memory for easily writing and erasing data or the like.

The terminal controller 210 may include a memory 213 configured to store and/or recall programs and data, and a processor 211 configured to process data according to the program stored in the memory 213 and control the user input/output unit 220, the terminal communicator 230, and the terminal storage 240.

The memory 213 may store a control program and control data for controlling operation of the user terminal 200, or may recall a user input received through the user input/output unit 220, communication data received through the terminal communicator 230, an application program loaded from the terminal storage 240, and the like.

The memory 213 may include a volatile memory such as an S-RAM and a D-RAM and a non-volatile memory such as a ROM, an EPROM, an EEPROM, and a flash memory.

The volatile memory, which is a memory that loses data stored therein when power is cut off, may temporarily store programs and data. The volatile memory may recall an application program or may recall the sleep data SD received from the sleep data acquisition apparatus 100.

The non-volatile memory, which is a memory capable of maintaining data stored therein even though power is cut off, may semi-permanently store programs and data. For example, the non-volatile memory may store a booting program and data for booting the user terminal 200 and the sleep data SD received from the sleep data acquisition apparatus 100.

The processor 211 may process data according to a program recalled in the memory 213 and control the user input/output unit 220, the terminal communicator 230, and the terminal storage 240 according to the processed data.

For example, the processor 211 may process the sleep data SD received through the terminal communicator 230 to generate sleep time information of the user. Also, the processor 211 may process the sleep time information of the user to generate sleep summary information of the user. Also, the processor 211 may output the sleep summary information of the user and a control signal to the user input/output unit 220 so that the sleep summary information can be displayed through the touch screen module 221.

As another example, the processor 211 may output the sleep data SD and a control signal to the terminal communicator 230 so that the sleep data SD can be transmitted to the sleep management server SV. Also, when the sleep information SI is received from the sleep management server SV, the processor 211 may obtain the sleep summary information from the sleep information SI. Also, the processor 211 may output the sleep summary information and a control signal to the user input/output unit 220 so that the sleep summary information can be displayed through the touch screen module 221.

As described above, the terminal controller 210 may control operation of the user input/output unit 220, the terminal communicator 230, and the terminal storage 240 included in the user terminal 200.

An operation of the user terminal 200, which will be described below, may be interpreted as being controlled by the terminal controller 210.

In particular, the control operation of the terminal controller 210 may be implemented as a sleep management application program. The user may download an application program through a WAN or a local area network (LAN). When the user executes the sleep management application program, the terminal controller 210 may execute a control operation that will be described below.

Configurations and operations of the sleep data acquisition apparatus 100 and the user terminal 200 included in the sleep management system 1 have been described above.

Interoperation between the sleep management system 1 and a home appliance will be described below.

FIG. 7 shows an example of communication between a sleep management system and home appliances according to an embodiment, and FIG. 8 shows another example of communication between a sleep management system and home appliances according to an embodiment.

As shown in FIGS. 7 and 8, the sleep data acquisition apparatus 100 may transmit sleep data SD obtained from a user to the user terminal 200 in a non-contact manner.

When the sleep data SD is received, the user terminal 200 may process the sleep data SD to determine a sleep state SS.

Also, the user terminal 200 may transmit controls signals CS1, CS2, and CS3 for controlling home appliances 300, 400, and 500 to the home appliances 300, 400, and 500 on the basis of the sleep state SS.

For example, the user terminal 200 may transmit a control signal for decreasing a volume of a sound output by an image display apparatus 300 or stopping operation of the image display apparatus 300 to the image display apparatus 300. Also, the user terminal 200 may transmit a control signal for changing an operation mode of an air conditioner 400 or changing a target temperature of the air conditioner 400 to the air conditioner 400. Also, the user terminal 200 may transmit a control signal for delaying operation of a refrigerator 500 to the refrigerator 500.

In this case, as shown in FIG. 7, the sleep data acquisition apparatus 100 and the user terminal 200 may communicate with each other on a one-to-one basis, and the user terminal 200 and the home appliances 300, 400, and 500 may communicate with each other on a one-to-one basis.

Also, as shown in FIG. 8, the sleep data acquisition apparatus 100, the user terminal 200, and the home appliances 300, 400, and 500 may form a LAN through an access point AP.

A detailed example of the interoperation between the sleep data acquisition apparatus 100, the user terminal 200, and the home appliances 300, 400, and 500 will be described below.

FIG. 9 shows an example of interoperation between a sleep management system and an image display apparatus according to an embodiment, and FIG. 10 shows operation of an image display apparatus during the interoperation shown in FIG. 9.

Interoperation 1000 between the sleep data acquisition apparatus 100, the user terminal 200, and the image display apparatus 300 will be described with reference to FIGS. 9 and 10.

The user terminal 200 receives the sleep data SD from the sleep data acquisition apparatus 100 (1005).

The sleep data acquisition apparatus 100 may detect a user's heart rate, respiration rate, and movement every predetermined time interval and transmit sleep data SD corresponding to the user's heart rate, respiration rate, and movement to the user terminal 200.

The sleep data acquisition apparatus 100 may transmit the sleep data SD to the user terminal 200 whenever the user's heart rate, respiration rate, and movement are detected or whenever a request for the sleep data SD is received from the user terminal 200 in addition to every predetermined time interval.

The user terminal 200 obtains a sleep state SS of the user on the basis of the sleep data SD (1010).

Also, the user terminal 200 may directly determine the sleep state SS of the user on the basis of the sleep data SD or may receive the sleep state SS through the sleep management server SV.

For example, the user terminal 200 may obtain the user's heart rate, respiration rate, and movement from the sleep data SD and determine whether the user lies on a bed, whether the user falls asleep, in which sleep stage the user is, whether the user wakes up briefly while sleeping, whether the user falls asleep again, whether the user completely wakes up, whether the user gets out of bed, and the like on the basis of the obtained heart rate, respiration rate, and movement.

As another example, the user terminal 200 may transmit the sleep data SD to the sleep management server SV and may receive the sleep state SS, such as whether the user lies on a bed, whether the user falls asleep, in which sleep stage the user is, whether the user wakes up briefly while sleeping, whether the user falls asleep again, whether the user completely wakes up, and whether the user gets out of bed, from the sleep management server SV.

The user terminal 200 determines whether the user falls asleep on the basis of the sleep state SS of the user (1020).

As described above, the user terminal 200 may obtain the sleep state SS of the user. In this case, the user terminal 200 may determine whether the sleep state SS of the user is changed from an awake state to an asleep state.

When the user is not asleep (no in 1020), the user terminal 200 repeatedly receives the sleep data SD and determines the sleep state of the user.

When the user is asleep (yes in 1020), the user terminal 200 determines whether a first time T1 passes (1030).

In detail, the user terminal 200 may determine whether the first time T1 passes after the user is detected as falling asleep (T0).

When the first time T1 does not pass (no in 1030), the user terminal 200 waits for the first time T1 to pass.

Sleep of the user may be disturbed by an external stimulus immediately after the user falls asleep. For example, when a volume of a sound output by the image display apparatus 300 changes immediately after the user falls asleep, the user may not fall asleep but may wake up due to the change in the sound volume.

In order to prevent the sleep of the user from being disturbed by an external stimulus, the user terminal 200 may wait for the first time T1 after the user is detected as falling asleep (T0).

When the first time T1 passes after the user falls asleep (yes in 1030), the user terminal 200 transmits a sound volume decrease command to the image display apparatus 300 (1035).

When a certain time (e.g., about five minutes) passes after the user falls asleep, the possibility of the sleep of the user being disturbed by a small external stimulus is low. Rather, there is a concern that the user may be interrupted from entering deep sleep by sounds output by the image display apparatus 300.

Accordingly, the user terminal 200 may transmit the sound volume decrease command to the image display apparatus 300 to decrease the volume of the sound output by the image display apparatus 300.

According to the sound volume decrease command of the user terminal 200, the image display apparatus 300 decreases the volume of the output sound (1037).

The image display apparatus 300 may decrease the volume of the output sound to a predetermined volume level (a value of "0" or higher) at once or step by step.

For example, as shown in FIG. 10, when the first time T1 passes after the user is detected as falling asleep (T0), the user terminal 200 may transmit the sound volume decrease command to the image display apparatus 300, and the image display apparatus 300 may decrease the volume of the output sound.

In addition, depending on the case, the image display apparatus 300 may decrease a brightness of an image output by the image display apparatus 300 in addition to decreasing the volume of the output sound.

Subsequently, the user terminal 200 determines whether a second time T2 passes (1040).

In detail, the user terminal 200 may determine whether the second time T2 passes after the user is detected as falling asleep (T0).

When the second time T2 does not pass (no in 1040), the user terminal 200 waits for the second time T2 to pass.

The sleep of the user may be disturbed by an external stimulus immediately after the user falls asleep. For example, when the image display apparatus 300 is turned off immediately after the user falls asleep, the user may not fall asleep but may be woken up by the image display apparatus 300 being turned off.

In order to prevent the sleep of the user from being disturbed by an external stimulus, the user terminal 200 may wait for the second time T2 after the user is detected as falling asleep (T0).

When the second time T2 passes after the user falls asleep (yes in 1040), the user terminal 200 transmits an operation stop command to the image display apparatus 300 (1045).

When a sufficient time (e.g., about 20 minutes) passes after the user falls asleep, the possibility of the sleep of the user being disturbed by a small external stimulus is low. Rather, there is a concern that the user may be interrupted from entering deep sleep by images and sounds output by the image display apparatus 300.

Accordingly, the user terminal 200 may transmit the operation stop command to the image display apparatus 300 to turn off the image display apparatus 300.

According to the operation stop command of the user terminal 200, the image display apparatus 300 stops operating (1047). That is, the image display apparatus 300 is turned off.

For example, as shown in FIG. 10, when the first time T2 passes after the user is detected as falling asleep (T0), the user terminal 200 may transmit the operation stop command to the image display apparatus 300, and the image display apparatus 300 may be turned off.

FIG. 11 shows another example of interoperation between a sleep management system and an image display apparatus according to an embodiment, and FIG. 12 shows operation of an image display apparatus during the interoperation shown in FIG. 11.

Interoperation 1100 between the sleep data acquisition apparatus 100, the user terminal 200, and the image display apparatus 300 will be described with reference to FIGS. 11 and 12.

The user terminal 200 receives the sleep data SD from the sleep data acquisition apparatus 100 (1105).

The sleep data acquisition apparatus 100 may detect a user's heart rate, respiration rate, and movement every predetermined time interval and transmit sleep data SD corresponding to the user's heart rate, respiration rate, and movement to the user terminal 200.

The user terminal 200 obtains a sleep state SS of the user on the basis of the sleep data SD (1110).

Also, the user terminal 200 may directly determine the sleep state SS of the user on the basis of the sleep data SD, or may receive the sleep state SS through the sleep management server SV. In detail, the user terminal 200 may obtain a sleep state, such as whether the user lies on a bed, whether the user falls asleep, in which sleep stage the user is, whether the user wakes up briefly while sleeping, whether the user falls asleep again, whether the user completely wakes up, and whether the user gets out of bed, on the basis of the sleep data SD.

The user terminal 200 determines whether the user wakes on the basis of the sleep state SS of the user (1120).

As described above, the user terminal 200 may obtain the sleep state SS of the user on the basis of the sleep data SD of the user. In this case, the user terminal 200 may determine whether the sleep state SS of the user is changed from the asleep state to the awake state.

Also, the user terminal 200 may determine whether the user wakes on the basis of a wake-up time preset by the user in conjunction with the sleep state SS of the user.

For example, when it is determined that the sleep state SS of the user is the awake state after the wake-up time preset by the user, the user terminal 200 may determine that the user is awake.

Also, when it is determined that the sleep state SS of the user is the awake state before the wake-up time preset by the user, the user terminal 200 determines whether the sleep state SS of the user is maintained as the awake state for a predetermined reference time or longer. When the sleep state SS of the user is maintained as the awake state for the predetermined reference time or longer, the user terminal 200 may determine that the user is awake. This is to provide a sufficient sleep time to the user before the wake-up time preset by the user.

When the user is not awake (no in 1120), the user terminal 200 repeatedly receives the sleep data SD and determines the sleep state of the user.

When the user is awake (yes in 1120), the user terminal 200 transmits an operation start command to the image display apparatus 300 (1125).

When the user wakes, an external stimulus may facilitate the waking of the user. Accordingly, the user terminal 200 may transmit the operation start command to the image display apparatus 300 to turn on the image display apparatus 300.

According to the operation start command of the user terminal 200, the image display apparatus 300 starts to operate (1127). That is, the image display apparatus 300 is turned on.

For example, as shown in FIG. 12, when the user wakes up, the user terminal 200 transmits the operation start command to the image display apparatus 300 and turns on the image display apparatus 300.

As described above, the user terminal 200 may determine the sleep state of the user or receive the sleep state of the user, and may control operation of the image display apparatus 300 according to the sleep state of the user.

FIG. 13 shows an example of interoperation between a sleep management system and an air conditioner according to an embodiment, and FIG. 14 shows an example of operation of the air conditioner during the interoperation shown in FIG. 13. Also, FIG. 15 shows an example of operation of the air conditioner in a sleep mode.

Interoperation 1200 between the sleep data acquisition apparatus 100, the user terminal 200, and the air conditioner 400 will be described with reference to FIGS. 13, 14, and 15.

The user terminal 200 receives the sleep data SD from the sleep data acquisition apparatus 100 (1205).

The sleep data acquisition apparatus 100 may detect a user's heart rate, respiration rate, and movement every predetermined time interval and transmit sleep data SD corresponding to the user's heart rate, respiration rate, and movement to the user terminal 200.

The user terminal 200 obtains a sleep state SS of the user on the basis of the sleep data SD (1210).

Also, the user terminal 200 may directly determine the sleep state SS of the user on the basis of the sleep data SD, or may receive the sleep state SS through the sleep management server SV. In detail, the user terminal 200 may obtain a sleep state, such as whether the user lies on a bed, whether the user falls asleep, in which sleep stage the user is, whether the user wakes up briefly while sleeping, whether the user falls asleep again, whether the user completely wakes up, and whether the user gets out of bed, on the basis of the sleep data SD.

The user terminal 200 determines whether the user falls asleep on the basis of the sleep state SS of the user (1220).

As described above, the user terminal 200 may obtain the sleep state SS of the user on the basis of the sleep data SD of the user. In this case, the user terminal 200 may determine whether the sleep state SS of the user is changed from the awake state to the asleep state.

When the user is not asleep (no in 1220), the user terminal 200 repeatedly receives the sleep data SD and determines the sleep state of the user.

When the user is asleep (yes in 1220), the user terminal 200 determines whether a first time T1 passes (1230).

When the first time T1 does not pass (no in 1230), the user terminal 200 waits for the first time T1 to pass.

Sleep of the user may be disturbed by an external stimulus immediately after the user falls asleep. For example, when the air conditioner 400 operates immediately after the user falls asleep, the user may not fall asleep but may wake due to the sudden operation of the air conditioner 400.

In order to prevent the sleep of the user from being disturbed by an external stimulus, the user terminal 200 may wait for the first time T1 after the user is detected as falling asleep (T0).

When the first time T1 passes after the user falls asleep (yes in 1230), the user terminal 200 transmits a sleep mode operation command to the air conditioner 400 (1235).

Properly adjusting an indoor temperature during sleep helps people sleep well. In order to properly adjust an indoor temperature while the user sleeps, the user terminal 200 may control the air conditioner 400. In detail, the user terminal 200 may control the air conditioner 400 so that the air conditioner 400 operates in a predetermined sleep mode. The sleep mode of the air conditioner 400 will be described in detail below.

According to the sleep mode operation command of the user terminal 200, the air conditioner 400 operates in the sleep mode (1237).

For example, as shown in FIG. 14, when the first time T1 passes after the user is detected as falling asleep (T0), the user terminal 200 may transmit the sleep mode operation command to the air conditioner 400, and the air conditioner 400 may operate in the sleep mode.

Here, the sleep mode is an operation mode of the air conditioner 400 in which an indoor temperature is properly adjusted while the user sleeps.

In particular, a target temperature of the air conditioner 400 may change according to a predetermined profile in the sleep mode, and the sleep mode may be divided into a plurality of stages according to a profile of the target temperature.

For example, as shown in FIG. 15, the sleep mode may include a sleep induction stage in which sleep of the user is induced, a sleep maintenance step in which the sleep of the user is maintained, and a wake-up inducing stage in which waking of the user is induced.

It is well known that people can easily fall asleep when an indoor temperature is low. Accordingly, in order to induce sleep of the user, the air conditioner 400 may quickly lower the indoor temperature to a predetermined sleep induction temperature in the sleep induction stage.

When the indoor temperature is too low during sleep, there is a concern that sleep of a person may be disturbed or the person may get a disease such as a cold. Accordingly, in order to maintain comfortable sleep of the user in a sleep maintenance stage, the air conditioner 400 may slowly increase the indoor temperature and maintain the indoor temperature at a predetermined sleep maintenance temperature when the indoor temperature reaches the sleep maintenance temperature. Also, in order to prevent the user from waking up briefly during sleep in the sleep maintenance stage, the air conditioner 400 may temporarily lower the indoor temperature.

When the wake-up time preset by the user is reached, the air conditioner 400 may increase the indoor temperature to a sleep stop temperature to induce waking of the user.

In this case, the sleep induction temperature, the sleep maintenance temperature, and the sleep stop temperature may be set by the user through the user terminal 200.

Like this, the air conditioner 400 may properly adjust the indoor temperature at the wake-up time preset by the user for comfortable sleep of the user.

In this case, the wake-up time may be set through the user terminal 200, and when the user falls asleep, the user terminal 200 may transmit the wake-up time preset by the user to the air conditioner 400 together with the sleep mode operation command.

FIG. 16 shows another example of interoperation between a sleep management system and an air conditioner according to an embodiment, and FIG. 17 shows operation of the air conditioner during the interoperation shown in FIG. 16.

Interoperation 1300 between the sleep data acquisition apparatus 100, the user terminal 200, and the air conditioner 400 will be described with reference to FIGS. 16 and 17.

The user terminal 200 receives the sleep data SD from the sleep data acquisition apparatus 100 (1305).

The sleep data acquisition apparatus 100 may detect a user's heart rate, respiration rate, and movement every predetermined time interval and transmit sleep data SD corresponding to the user's heart rate, respiration rate, and movement to the user terminal 200.

The user terminal 200 obtains a sleep state SS of the user on the basis of the sleep data SD (1310).

Also, the user terminal 200 may directly determine the sleep state SS of the user on the basis of the sleep data SD, or may receive the sleep state SS through the sleep management server SV. In detail, the user terminal 200 may obtain a sleep state, such as whether the user lies on a bed, whether the user falls asleep, in which sleep stage the user is, whether the user wakes up briefly while sleeping, whether the user falls asleep again, whether the user completely wakes up, and whether the user gets out of bed, on the basis of the sleep data SD.

The user terminal 200 determines whether the user wakes on the basis of the sleep state SS of the user (1320).

In this case, the user terminal 200 may determine whether the user wakes on the basis of a wake-up time preset by the user in conjunction with the sleep state SS of the user.

For example, when it is determined that the sleep state SS of the user is the awake state after the wake-up time preset by the user, the user terminal 200 may determine that the user is awake.

Also, when it is determined that the sleep state SS of the user is the awake state before the wake-up time preset by the user, the user terminal 200 determines whether the sleep state SS of the user is maintained as the awake state for a predetermined reference time or longer. When the sleep state SS of the user is maintained as the awake state for the predetermined reference time or longer, the user terminal 200 may determine that the user is awake. This is to provide a sufficient sleep time to the user before the wake-up time preset by the user.

When the user is not awake (no in 1320), the user terminal 200 repeatedly receives the sleep data SD and determines the sleep state of the user.

When the user is awake (yes in 1320), the user terminal 200 transmits a normal mode operation command to the air conditioner 400 (1325).

When the user wakes, it is necessary to switch the operation mode of the air conditioner 400 from a sleep mode to a normal mode to provide a comfortable indoor temperature to the user who is awake. Accordingly, the user terminal 200 may transmit the normal mode operation command to the air conditioner 400 so that the operation mode of the air conditioner 400 is changed to the normal mode.

According to the normal mode operation command of the user terminal 200, the air conditioner 400 changes the operation mode from the sleep mode to the normal mode (1327).

For example, as shown in FIG. 17, when the user wakes, the user terminal 200 transmits the normal mode operation command to the air conditioner 400, and the air conditioner 400 operates in the normal mode.

Subsequently, the user terminal 200 determines whether the user gets out of bed (1330).

In detail, the user terminal 200 may receive the sleep data SD from the sleep data acquisition apparatus 100 and obtain the sleep state SS of the user on the basis of the received sleep data SD.

Also, the user terminal 200 may determine whether the user gets out of bed on the basis of the sleep state SS of the user.

When the user gets out of bed (yes in 1330), the user terminal 200 transmits an operation stop command to the air conditioner 400 (1335).

When the user gets out of bed, the user terminal 200 may determine that the user no longer wants to continue sleeping, and thus may stop the operation of the air conditioner 400.

Accordingly, the user terminal 200 may transmit the operation stop command to the air conditioner 400 to turn off the air conditioner 400.

According to the operation stop command of the user terminal 200, the air conditioner 400 stops operating (1337). That is, the air conditioner 400 is turned off.

For example, as shown in FIG. 17, when the user wakes up, the user terminal 200 transmits the operation stop command to the air conditioner 400, and the air conditioner 400 is turned off.

As described above, the user terminal 200 may determine the sleep state of the user or receive the sleep state of the user, and may control operation of the air conditioner 400 according to the sleep state of the user.

As described above, the user terminal 200 may display the sleep information SI (more particularly, sleep summary information) of the user according to a user input, and may preset operation of the home appliances 300, 400, and 500 to be performed during sleep.

Also, the user terminal 200 may display a graphic user interface for displaying the sleep information SI of the user and presetting the operation of the home appliances 300, 400, and 500.

The graphic user interface displayed on the user terminal 200 will be described below.

FIG. 18 shows an example of a sleep information display screen displayed on a user terminal according to an embodiment.

A sleep information display screen 2001 shown in FIG. 18 may be displayed on the user terminal 200 according to a user input.

A plurality of menus 2100, 2200, 2300, and 2400 for selecting information displayed on the user terminal 200 may be displayed at one side of the sleep information display screen 2001.

In detail, the plurality of menus 2100, 2200, 2300, and 2400 include a sleep summary menu 2100 for displaying sleep summary information, a daily sleep summary menu 2200 for displaying sleep summary information associated with the current date, a monthly sleep summary menu 2300 for displaying sleep summary information associated with a month of the current date, and a home appliance menu 2400 for setting operation of a home appliance. When the user touches one of the menus 2100, 2200, 2300, and 2400, a screen corresponding to the touched menu may be displayed.

Also, the sleep summary information 2120 may be displayed at the one side of the sleep information display screen 2001.

The sleep summary information 2120 is generated by processing some of the sleep information so that the user can check his or her sleep quality. For example, the sleep summary information 2120 may include a total sleep time, a time it takes the user to fall asleep, the number of times the user wakes-up while sleeping, sleep efficiency, a deep sleep time, an REM sleep time, or the like of the user.

Also, a sleep score 2110 may be displayed at the one side of the sleep information display screen 2001.

The sleep score 2110 represents the sleep summary information 2120 in numerical form. In detail, in order to calculate the sleep score 2110, the user terminal 200 may represent items included in the sleep summary information 2120 in numerical form as numbers, weight the numbers, and then sum the weighted numbers.

The user may quantitatively confirm his or her sleep quality through the sleep score 2110.

Also, an alarm time setting menu 2500 for setting a wake-up time and a sleep environment setting menu 2600 for generally setting a sleep environment may be displayed at the one side of the sleep information display screen 2001.

FIG. 19 shows an example of a home appliance setting screen displayed on a user terminal according to an embodiment. Also, FIG. 20 shows an example of an air conditioner setting screen displayed on a user terminal according to an embodiment, and FIG. 21 shows an example of an image display apparatus setting screen display on a user terminal according to an embodiment.

When a user touches the home appliance setting menu 2400 (see FIG. 18) displayed in the sleep information display screen 2001 (see FIG. 18), the user terminal 200 may display a home appliance setting screen 2401 shown in FIG. 19.

An air conditioner setting menu 2410 for setting operation of an air conditioner, an image display apparatus setting menu 2420 for setting operation of an image display apparatus, and a thermostat setting menu 2430 for setting operation of a thermostat may be displayed at one side of the home appliance setting screen 2401.

When a user touches the air conditioner setting menu 2410, the user terminal 200 may display an air conditioner setting screen 2411 shown in FIG. 20.

The user may set an indoor temperature and an air volume to be applied during sleep through the air conditioner setting screen 2411.

In detail, the air conditioner setting screen 2411 may include a temperature setting region 2413 for setting an indoor temperature during sleep of the user, an air volume setting region 2415 for setting an air volume during the user's sleep, and a storage command region 2417 for storing the set indoor temperature and the set air volume.

A target indoor temperature set by the user is displayed in the temperature setting region 2413, and the user terminal 200 may raise or lower the target indoor temperature according to a touch input of the user that is input through the temperature setting region 2413.

Also, an air volume set by the user is displayed in the air volume setting region 2415, and the user terminal 200 may raise or lower the air volume according to a touch input of the user that is input through the air volume setting region 2415.

Also, the user terminal 200 may store the indoor temperature and the air volume that are set by the user according to a touch input of the user that is input through the storage command region 2417.

The indoor temperature and the air volume that are set by the user may be transmitted to the air conditioner in the sleep state SS of the user.

For example, when the user falls asleep, the user terminal 200 may transmit the indoor temperature and the air volume that are set by the user to the air conditioner, and the air conditioner may operate according to the received indoor temperature and air volume.

When the user touches the image display apparatus setting menu 2420, the user terminal 200 may display an image display apparatus setting screen 2421 shown in FIG. 21.

Through the image display apparatus setting screen 2421, the user may set operation of the image display apparatus to be performed during sleep.

In detail, a turn-off setting menu 2425 for turning off the image display apparatus while the user sleeps and a turn-off cancellation menu 2423 for preventing the image display apparatus from being turned off while the user sleeps may be displayed in the image display apparatus setting screen 2421, and the user may select one of the turn-off setting menu 2425 and the turn-off cancellation menu 2423.

When the turn-off setting menu 2425 is selected, the user terminal 200 may transmit an operation stop command for turning off the image display apparatus to the image display apparatus while the user sleeps.

Also, when the turn-off cancellation menu 2423 is selected, the user terminal 200 may not transmit the operation stop command to the image display apparatus even though the user is sleeping.

As described above, the user may individually set operation of a home appliance through a graphic user interface displayed on the user terminal 200.

In addition, the user may collectively set operations of a plurality of home appliances through the graphic user interface displayed on the user terminal 200.

FIG. 22 shows an example of a sleep environment setting screen displayed on a user terminal according to an embodiment, and FIG. 23 shows an example of an indoor temperature setting screen displayed on a user terminal according to an embodiment. Also, FIG. 24 shows a change in indoor temperature caused by the indoor temperature setting screen shown in FIG. 23.

When a user touches the sleep environment setting menu 2600 (see FIG. 18) displayed in the sleep information display screen 2001 (see FIG. 18), the user terminal 200 may display a sleep environment setting screen 2601 shown in FIG. 22.

An image display apparatus setting region 2610 for setting operation of an image display apparatus during sleep of the user, an air conditioner setting region 2620 for setting operation of an air conditioner during the user's sleep, and a thermostat setting region 2630 for setting operation of a thermostat during the user's sleep may be displayed in the sleep environment setting screen 2601.

A turn-off setting menu 2613 for turning off the image display apparatus while the user sleeps and a turn-off cancellation menu 2611 for preventing the image display apparatus from being turned off while the user sleeps may be displayed in the image display apparatus setting region 2610, and the user may select one of the turn-off setting menu 2613 and the turn-off cancellation menu 2611.

When the turn-off setting menu 2613 is selected, the user terminal 200 may transmit an operation stop command for turning off the image display apparatus to the image display apparatus while the user sleeps. Also, when the turn-off cancellation menu 2611 is selected, the user terminal 200 may not transmit the operation stop command to the image display apparatus even though the user is sleeping.

Also, a sleep mode cancellation menu 2621 for canceling sleep mode operation of the air conditioner while the user sleeps, an automatic sleep mode menu 2623 for enabling the air conditioner to operate in a predetermined sleep mode while the user sleeps, and a user sleep mode menu 2625 for enabling the air conditioner to operate in a sleep mode set by the user while the user sleeps may be displayed in the air conditioner setting region 2620. Also, the user may select any one of the sleep mode cancellation menu 2621, the automatic sleep mode menu 2623, and the user sleep mode menu 2625.

When the sleep mode cancellation menu 2621 is selected, the user terminal 200 does not control operation of the air conditioner even though the user's sleep is detected. In other words, the air conditioner continues operating even though the user falls asleep.

When the automatic sleep mode menu 2623 is selected, the user terminal 200 may transmit a sleep mode operation command to the air conditioner in response to the user falling asleep. Also, the air conditioner may operate in the sleep mode according to the sleep mode operation command of the user terminal 200. In this case, the air conditioner may operate in the sleep mode according to a predetermined sleep induction temperature, sleep maintenance temperature, and sleep stop temperature.

When the user sleep mode menu 2625 is selected, the user terminal 200 may display a sleep temperature setting screen 2640 for setting the sleep induction temperature, the sleep maintenance temperature, and the sleep stop temperature for the sleep mode, as shown in FIG. 23.

The sleep temperature setting screen 2640 may include a sleep induction setting region 2641 for setting an indoor temperature (the sleep induction temperature) and an air volume (a sleep induction air volume) in the sleep induction stage of the sleep mode, a sleep maintenance setting region 2643 for setting an indoor temperature (the sleep maintenance temperature) and an air volume (a sleep maintenance air volume) in the sleep maintenance stage of the sleep mode, and a sleep stop setting region 2645 for setting an indoor temperature (the sleep stop temperature) and an air volume (a sleep stop air volume) in a sleep stop stage of the sleep mode.

The sleep induction setting region 2641 may include an induction temperature setting region 2641a for setting an indoor temperature in the sleep induction stage, and an induction air volume setting region 2641b for setting an air volume in the sleep induction stage.

The sleep induction temperature set by the user may be displayed in the induction temperature setting region 2641a, and the user terminal 200 may raise or lower the sleep induction temperature according to a touch input of the user that is input through the induction temperature setting region 2641a. Also, an air volume set by the user is displayed in the induction air volume setting region 2641b, and the user terminal 200 may raise or lower the sleep induction air volume according to a touch input of the user that is input through the induction air volume setting region 2641b.

The sleep maintenance setting region 2643 may include a maintenance temperature setting region 2643a for setting an indoor temperature in the sleep maintenance stage, and a maintenance air volume setting region 2643b for setting an air volume in the sleep maintenance stage.

The sleep maintenance temperature set by the user may be displayed in the maintenance temperature setting region 2643a, and the user terminal 200 may raise or lower the sleep maintenance temperature according to a touch input of the user that is input through the maintenance temperature setting region 2643a. Also, an air volume set by the user is displayed in the maintenance air volume setting region 2643b, and the user terminal 200 may raise or lower the sleep maintenance air volume according to a touch input of the user that is input through the maintenance air volume setting region 2643b.

The sleep stop setting region 2645 may include a stop temperature setting region 2645a for setting an indoor temperature in the sleep stop stage, and a stop air volume setting region 2645b for setting an air volume in the sleep stop stage.

The sleep stop temperature set by the user is displayed in the stop temperature setting region 2645a, and the user terminal 200 may raise or lower the sleep stop temperature according to a touch input of the user that is input through the stop temperature setting region 2645a. Also, an air volume set by the user is displayed in the stop air volume setting region 2645b, and the user terminal 200 may raise or lower the sleep stop air volume according to a touch input of the user that is input through the stop air volume setting region 2645b.

For example, as shown in FIG. 23, the user may set the sleep induction temperature, the sleep maintenance temperature, and the sleep stop temperature to be 23° C., 25° C., and 24° C., respectively.

As a result, the indoor temperature may change while the user sleeps, as shown in FIG. 24. In detail, the indoor temperature may be maintained at 23° C., which is set by the user, in the sleep induction stage, and the indoor temperature may be slowly increased and maintained at 25° C., which is set by the user, in the sleep maintenance stage. Also, the indoor temperature may be 24° C., which is set by the user, in the sleep stop stage.

As described above, the user terminal 200 may receive a user input for setting operation of the home appliances 300, 400, and 500 from the user, and may control the operation of the home appliances 300, 400, and 500 according to the user input.

The sleep management system 1 including the sleep data acquisition apparatus 100 and the user terminal 200 according to an embodiment has been described above.

A sleep management system according to another embodiment will be described below.

FIG. 25 shows an example of communication between a sleep management system and home appliances according to another embodiment, and FIG. 26 shows another example of communication between a sleep management system and home appliances according to another embodiment.

As shown in FIGS. 25 and 26, a sleep management system 2 according to another embodiment may include a sleep data acquisition apparatus 100 and at least one home appliance 300, 400, or 500.

The sleep data acquisition apparatus 100 may collect sleep data SD of a user while the user is sleeping, falling asleep, or waking up, as described above. Also, the sleep data acquisition apparatus 100 may transmit the sleep data SD of the user to the at least one home appliance 300, 400, or 500.

In detail, the at least one home appliance 300, 400, or 500 may receive the sleep data SD of the user from the sleep data acquisition apparatus 100 and may obtain a sleep state SS of the user on the basis of the received sleep data SD.

For example, the at least one home appliance 300, 400, or 500 may obtain a sleep state SS of a user U. In detail, the user terminal 200 may determine whether the user U is lying on a bed B, whether the user U falls asleep, in which sleep stage the user U is, whether the user U wakes up briefly while sleeping, whether the user U falls asleep again, whether the user U completely wakes up, whether the user U gets out of the bed B, and the like.

Also, the at least one home appliance 300, 400, or 500 may perform a predetermined operation according to the sleep state SS of the user.

However, the configuration of the sleep management system 2 is not limited to that shown in FIG. 25.

For example, as shown in FIG. 26, the sleep management system 2 may further include a sleep management server SV in addition to the sleep data acquisition apparatus 100 and the at least one home appliance 300, 400, or 500.

In detail, the sleep data acquisition apparatus 100 and the at least one home appliance 300, 400, or 500 may form a LAN through an access point AP. Also, the access point AP may be connected to the sleep management server SV via a WAN.

The sleep management server SV may receive the sleep data SD from the sleep data acquisition apparatus 100, process the received sleep data SD, and generate the sleep state SS or sleep information SI of the user U. Also, the sleep management server SV may transmit the sleep state SS or the sleep information SI of the user U to the at least one home appliance 300, 400, or 500.

In other words, when the sleep data SD is obtained, the sleep data acquisition apparatus 100 may transmit the obtained sleep data SD to the sleep management server SV, and the at least one home appliance 300, 400, or 500 may receive the sleep state SS or the sleep information SI of the user U from the sleep management server SV.

In particular, the sleep management server SV may obtain sleep data of a plurality of users from a plurality of sleep data acquisition apparatuses, process the sleep data, and generate sleep information of the plurality of users. In this case, the sleep management server SV may manage the sleep information of the plurality of users on a user basis.

In addition, the sleep management server SV may manage the sleep information SI of the plurality of users on a group basis, wherein the groups are set by the users. For example, when the plurality of users are set as family members, the sleep management server SV may transmit sleep information of the family members (the plurality of users) to user terminals of the family members so that the family members can share the sleep information.

A detailed example of interoperation between the sleep data acquisition apparatus 100 and the home appliances 300, 400, and 500 will be described below.

FIG. 27 shows an example of operation of an image display apparatus included in a sleep management system according to another embodiment.

Operation 3000 of an image display apparatus 300 will be described with reference to FIG. 27.

The image display apparatus 300 obtains a sleep state SS of a user (3010).

The sleep data acquisition apparatus 100 may detect a heart rate, respiration rate, and movement of the user every predetermined time interval and transmit sleep data SD corresponding to the user's heart rate, respiration rate, and movement to the image display apparatus 300 or the sleep management server SV.

In this case, the image display apparatus 300 may directly determine the sleep state SS, or may obtain the sleep state SS from the sleep management server SV.

When the sleep data acquisition apparatus 100 transmits the sleep data SD to the image display apparatus 300, the image display apparatus 300 may obtain the user's heart rate, respiration rate, and movement from the sleep data SD and determine whether the user lies on a bed, whether the user falls asleep, in which sleep stage the user is, whether the user wakes up briefly while sleeping, whether the user falls asleep again, whether the user completely wakes up, whether the user gets out of the bed, and the like on the basis of the obtained heart rate, respiration rate, and movement.

When the sleep data acquisition apparatus 100 transmits the sleep data SD to the sleep management server SV, the image display apparatus 300 may receive a sleep state SS, such as whether the user lies on a bed, whether the user falls asleep, in which sleep stage the user is, whether the user wakes up briefly while sleeping, whether the user falls asleep again, whether the user completely wakes up, whether the user gets out of the bed, and the like from the sleep management server SV.

The image display apparatus 300 determines whether the user falls asleep on the basis of the sleep state SS of the user (3020).

As described above, the image display apparatus 300 may obtain the sleep state SS of the user. In this case, the image display apparatus 300 may determine whether the sleep state SS of the user is changed from an awake state to an asleep state.

When the user does not fall asleep (no in 3020), the image display apparatus 300 repeatedly determines the sleep state SS of the user.

When the user falls asleep (yes in 3020), the image display apparatus 300 determines whether a first time passes (3030).

In detail, the image display apparatus 300 may determine whether the first time passes after the user is detected as falling asleep.

When the first time does not pass (no in 3030), the image display apparatus 300 waits for the first time to pass.

Sleep of the user may be disturbed by an external stimulus immediately after the user falls asleep. For example, when a volume of a sound output by the image display apparatus 300 changes immediately after the user falls asleep, the user may not fall asleep but may wake due to the change in the sound volume.

In order to prevent the sleep of the user from being disturbed by an external stimulus, the image display apparatus 300 may wait for the first time after the user is detected as falling asleep.

When the first time passes after the user falls asleep (yes in 3030), the image display apparatus 300 lowers the volume (3035).

When a certain time (e.g., about five minutes) passes after the user falls asleep, the possibility of the sleep of the user being disturbed by a small external stimulus is low. Rather, there is a concern that the user may be interrupted from entering deep sleep by sounds output by the image display apparatus 300.

Accordingly, the image display apparatus 300 may decrease the volume of the output sound to a predetermined volume level (a value of "0" or higher) at once or step by step.

In addition, depending on the case, the image display apparatus 300 may decrease a brightness of an image output by the image display apparatus 300 as well as decreasing the volume of the output sound.

Subsequently, the image display apparatus 300 determines whether a second time passes (3040).

In detail, the image display apparatus 300 may determine whether the second time passes after the user is detected as falling asleep.

When the second time does not pass (no in 3040), the image display apparatus 300 waits for the second time to pass.

The sleep of the user may be disturbed by an external stimulus immediately after the user falls asleep. For example, when the image display apparatus 300 is turned off immediately after the user falls asleep, the user may not fall asleep but may wake due to the image display apparatus 300 being turned off.

In order to prevent the sleep of the user from being disturbed by an external stimulus, the image display apparatus 300 may wait for the second time after the user is detected as falling asleep.

When the second time passes after the user falls asleep (yes in 3040), the image display apparatus 300 stops operating (3045). That is, the image display apparatus 300 is turned off.

When a sufficient time (e.g., about 20 minutes) passes after the user falls asleep, the possibility of the sleep of the user being disturbed by a small external stimulus is low. Rather, there is a concern that the user may be interrupted from entering deep sleep by images and sounds output by the image display apparatus 300. Accordingly, the image display apparatus 300 is turned off.

FIG. 28 shows another example of operation of an image display apparatus included in a sleep management system according to another embodiment.

Operation 3100 of the image display apparatus 300 will be described with reference to FIG. 28.

The image display apparatus 300 obtains a sleep state SS of a user (3110).

The sleep data acquisition apparatus 100 may detect a heart rate, respiration rate, and movement of the user every predetermined time interval and transmit sleep data SD corresponding to the user's heart rate, respiration rate, and movement to the image display apparatus 300 or the sleep management server SV.

In this case, the image display apparatus 300 may directly determine the sleep state SS, or may obtain the sleep state SS from the sleep management server SV.

The image display apparatus 300 determines whether the user wakes on the basis of the sleep state SS of the user (3120).

As described above, the image display apparatus 300 may obtain the sleep state SS of the user. In this case, the image display apparatus 300 may determine whether the sleep state SS of the user is changed from the asleep state to the awake state.

Also, the image display apparatus 300 may determine whether the user wakes on the basis of a wake-up time preset by the user in conjunction with the sleep state SS of the user.

For example, when it is determined that the sleep state SS of the user is the awake state after the wake-up time preset by the user, the image display apparatus 300 may determine that the user is awake.

Also, when it is determined that the sleep state SS of the user is the awake state before the wake-up time preset by the user, the image display apparatus 300 determines whether the sleep state SS of the user is maintained as the awake state for a predetermined reference time or longer. When the sleep state SS of the user is maintained as the awake state for the predetermined reference time or longer, the image display apparatus 300 may determine that the user is awake. This is to provide a sufficient sleep time to the user before the wake-up time preset by the user.

When the user does not wake up (no in 3120), the image display apparatus 300 repeatedly determines the sleep state SS of the user.

When the user wakes up (yes in 3120), the image display apparatus 300 starts to operate (3125). That is, the image display apparatus 300 is turned on.

When the user wakes, an external stimulus may facilitate waking of the user. Accordingly, the image display apparatus 300 is turned on.

As described above, the image display apparatus 300 may determine the sleep state of the user or receive the sleep state of the user and may operate according to the sleep state of the user.

FIG. 29 shows an example of operation of an air conditioner included in a sleep management system according to another embodiment.

Operation 3200 of an air conditioner 400 will be described with reference to FIG. 29.

The air conditioner 400 obtains a sleep state SS of a user (3210).

The sleep data acquisition apparatus 100 may detect a heart rate, respiration rate, and movement of the user every predetermined time interval and transmit sleep data SD corresponding to the user's heart rate, respiration rate, and movement to the air conditioner 400 or the sleep management server SV.

In this case, the air conditioner 400 may directly determine the sleep state SS, or may obtain the sleep state SS from the sleep management server SV.

The air conditioner 400 determines whether the user falls asleep on the basis of the sleep state SS of the user (3220).

As described above, the air conditioner 400 may obtain the sleep state SS of the user. In this case, the air conditioner 400 may determine whether the sleep state SS of the user is changed from the awake state to the asleep state.

When the user does not fall asleep (no in 3220), the air conditioner 400 repeatedly determines the sleep state SS of the user.

When the user falls asleep (yes in 3220), the air conditioner 400 determines whether a first time passes (3230).

In detail, the air conditioner 400 may determine whether the first time passes after the user is detected as falling asleep.

When the first time does not pass (no in 3230), the air conditioner 400 waits for the first time to pass.

Sleep of the user may be disturbed by an external stimulus immediately after the user falls asleep. For example, when the air conditioner 400 operates immediately after the user falls asleep, the user may not fall asleep but may wake due to the sudden operation of the air conditioner 400.

In order to prevent the sleep of the user from being disturbed by an external stimulus, the air conditioner 400 may wait for the first time after the user is detected as falling asleep.

When the first time passes after the user falls asleep (yes in 3230), the air conditioner 400 operates in a sleep mode (3235).

Properly adjusting an indoor temperature during sleep helps people sleep well. In order to properly adjust an indoor temperature while the user sleeps, the air conditioner 400 may operate in a predetermined sleep mode.

Here, the sleep mode is an operation mode of the air conditioner 400 in which the indoor temperature is properly adjusted while the user sleeps.

In particular, a target temperature of the air conditioner 400 may change according to a predetermined profile in the sleep mode, and the sleep mode may be divided into a plurality of stages according to a profile of the target temperature. For example, the sleep mode may include a sleep induction stage in which sleep of the user is induced, a sleep maintenance step in which the sleep of the user is maintained, and a wake-up induction stage in which waking of the user is induced.

FIG. 30 shows another example of operation of an air conditioner included in a sleep management system according to another embodiment.

Operation 3300 of an image display apparatus 300 will be described with reference to FIG. 30.

An air conditioner 400 obtains a sleep state SS of a user (3310).

A sleep data acquisition apparatus 100 may detect a heart rate, respiration rate, and movement of the user every predetermined time interval and transmit sleep data SD corresponding to the user's heart rate, respiration rate, and movement to the image display apparatus 300 or a sleep management server SV.

In this case, the air conditioner 400 may directly determine the sleep state SS, or may receive the sleep state SS from the sleep management server SV.

The air conditioner 400 determines whether the user wakes on the basis of the sleep state SS of the user (3320).

As described above, the air conditioner 400 may obtain the sleep state SS of the user. In this case, the air conditioner 400 may determine whether the sleep state SS of the user is changed from an asleep state to an awake state.

Also, the air conditioner 400 may determine whether the user wakes on the basis of a wake-up time preset by the user in conjunction with the sleep state SS of the user.

For example, when it is determined that the sleep state SS of the user is the awake state after the wake-up time preset by the user, the air conditioner 400 may determine that the user is awake.

Also, when it is determined that the sleep state SS of the user is the awake state before the wake-up time preset by the user, the air conditioner 400 determines whether the sleep state SS of the user is maintained as the awake state for a predetermined reference time or longer. When the sleep state SS of the user is maintained as the awake state for the predetermined reference time or longer, the air conditioner 400 may determine that the user is awake. This is to provide a sufficient sleep time to the user before the wake-up time preset by the user.

When the user does not wake up (no in 3320), the air conditioner 400 repeatedly determines the sleep state SS of the user.

When the user wakes up (yes in 3320), the air conditioner 400 switches an operation mode from a sleep mode to a normal mode (3325).

When the user wakes up, it is necessary to switch the operation mode of the air conditioner 400 from the sleep mode to the normal mode to provide a comfortable indoor temperature to the user who is awake. Accordingly, the air conditioner 400 may be switched to the normal mode.

Subsequently, the air conditioner 400 determines whether the user gets out of bed (3330).

In detail, the air conditioner 400 may directly determine the sleep state SS, or may receive the sleep state SS from the sleep management server SV. Also, the air conditioner 400 may determine whether the user gets out of bed on the basis of the sleep state SS of the user.

When the user gets out of bed (yes in 3330), the air conditioner 400 stops operating (3335). That is, the air conditioner 400 is turned off.

When the user gets out of bed, the user terminal 200 may determine that the user no longer wants to continue sleeping, and thus may stop the operation of the air conditioner 400. Accordingly, the air conditioner 400 is turned off.

As described above, the air conditioner 400 may determine or receive the sleep state of the user, and operate according to the sleep state of the user.

While embodiments of the present disclosure has been particularly shown and described, it should be understood by those skilled in the art that various changes in form and details may be made therein without departing from the spirit and scope of the disclosure as defined by the appended claims, and also the various changes are not to be understood as departing from the spirit and scope of the present disclosure.

The invention claimed is:

1. A user terminal comprising:
 a communicator configured to communicate with a sleep data acquisition apparatus and at least one home appliance;
 a display configured to display a graphic user interface comprising a sleep environment setting screen for setting a sleep environment setting for controlling operation of the at least one home appliance, wherein the sleep environment setting includes an air volume setting for a sleep induction stage for inducing a sleep of a user, a first air volume setting for a sleep maintenance stage for maintaining the sleep of the user, and a second air volume setting for a sleep stop stage for stopping the sleep of the user;
 a controller configured to:
  receive and store the sleep environment setting from the user through the graphic user interface,
  receive sleep data from the sleep data acquisition apparatus through the communicator, wherein the sleep data includes signals corresponding to a heart rate, respiration rate, and movement of the user detected by a piezoelectric sensor,
  obtain a sleep state or an awake state of the user based on the sleep data,
  obtain a bed occupancy status of the user based on the sleep data,
  transmit a control signal based on the sleep state or the awake state of the user and the bed occupancy status of the user to the at least one home appliance through the communicator,
  control, in response to the user being in the sleep state, the at least one home appliance according to the sleep environment setting, and control, in response to the user being in the awake state before a predetermined wake-up time, the at least one home appliance according to an awake state setting, wherein to determine the awake state, the controller is configured to determine whether the awake state has been maintained by the user for at least a predetermined time duration, and confirm the user as being in the awake state when the awake state has been maintained by the user for at least the predetermined time duration.

2. The user terminal of claim 1, wherein the controller is further configured to:
   obtain, from the sleep data:
   a first signal corresponding to the heart rate of the user,
   a second signal corresponding to the respiration rate of the user, and
   a third signal corresponding to the movement of the user, and
   identify the sleep state or the awake state of the user based on the obtained first signal, second signal, and third signal.

3. The user terminal of claim 1, wherein the controller is further configured to:
   transmit the sleep data to a sleep management server using the communicator, and
   receive the sleep state or the awake state of the user from the sleep management server by using the communicator.

4. The user terminal of claim 1, wherein the graphic user interface includes a sleep information display screen for displaying at least one of:
   a total sleep time,
   a time it takes the user to fall asleep,
   a number of times the user wakes up while sleeping,
   sleep efficiency,
   a deep sleep time, or
   a rapid eye movement sleep time of the user.

5. The user terminal of claim 1,
   wherein the sleep environment setting further includes an indoor temperature setting for while the user is asleep, and
   wherein in response to determining the user is asleep, the controller is configured to:
      transmit the indoor temperature setting to the at least one home appliance using the communicator, and
      switch an operation mode of the at least one home appliance.

6. The user terminal of claim 1, wherein the sleep environment setting further includes a sleep induction temperature setting for inducing the sleep of the user, a sleep maintenance temperature setting for maintaining the sleep of the user, and a sleep stop temperature setting for stopping the sleep of the user, and
   wherein the controller is configured to:
      transmit the sleep induction temperature, the sleep maintenance temperature, and the sleep stop temperature setting to the at least one home appliance, and
      switch an operation mode of the at least one home appliance based on the sleep state of the user.

7. The user terminal of claim 1, wherein the sleep environment setting further includes a setting for selecting whether to turn off the at least one home appliance while the user is asleep, and
   wherein the controller is configured to transmit an operation stop command to the at least one home appliance for turning off the at least one home appliance when the user is determined to be asleep.

\* \* \* \* \*